(12) United States Patent
Birch et al.

(10) Patent No.: US 10,466,082 B2
(45) Date of Patent: Nov. 5, 2019

(54) FLOW METER

(71) Applicant: University of Surrey, Guildford Surrey (GB)

(72) Inventors: David Birch, Guildford Surrey (GB); Paul Nathan, Guildford Surrey (GB); Praveen Rampersad, Cunupia (TT)

(73) Assignee: University of Surrey, Guildford (GB)

(*) Notice: Subject to any disclaimer, the term of this patent is extended or adjusted under 35 U.S.C. 154(b) by 84 days.

(21) Appl. No.: 15/542,129

(22) PCT Filed: Dec. 21, 2015

(86) PCT No.: PCT/GB2015/054101
§ 371 (c)(1),
(2) Date: Jul. 7, 2017

(87) PCT Pub. No.: WO2016/110668
PCT Pub. Date: Jul. 14, 2016

(65) Prior Publication Data
US 2018/0259380 A1    Sep. 13, 2018

(30) Foreign Application Priority Data

Jan. 8, 2015  (GB) .................................. 1500257.9

(51) Int. Cl.
| | | |
|---|---|---|
| *G01F 1/46* | (2006.01) | |
| *A61B 5/087* | (2006.01) | |
| *G01F 1/44* | (2006.01) | |

(52) U.S. Cl.
CPC ............... *G01F 1/46* (2013.01); *A61B 5/087* (2013.01); *G01F 1/44* (2013.01)

(58) Field of Classification Search
USPC ........................................ 73/861.61, 861.65
See application file for complete search history.

(56) References Cited

U.S. PATENT DOCUMENTS

| 2,617,301 A | 11/1952 | Gentile, Jr. |
| 3,035,569 A * | 5/1962 | Felkel .................... A61B 5/087 |
| | | 600/531 |

(Continued)

FOREIGN PATENT DOCUMENTS

| CN | 202281781 U | 6/2012 |
| EP | 0651971 A1 | 5/1995 |

(Continued)

OTHER PUBLICATIONS

Linda M. Huffman "AANA Journal Course: New Technologies in Anesthesia: Update for Nurse Anesthetists—Monitoring Ventilation and Compliance with Side Stream Spirometry" Journal of the American Association of Nurse Anesthetists—Jun. 1991, vol. 59, No. 3, pp. 249-258, Texas.

(Continued)

*Primary Examiner* — Clayton E. LaBalle
*Assistant Examiner* — Warren K Fenwick
(74) *Attorney, Agent, or Firm* — Nelson Mullins Riley & Scarborough LLP; Anthony A. Laurentano

(57) ABSTRACT

A flow meter (1) comprising a sampling tube (3) through which fluid may flow and a sensor arrangement (9, 25, 27, 39, 41, 43, 44, 45, 46, 47), wherein the sampling tube (3) comprises a first hollow section (51, 53) having a first internal cross-sectional area ($A_1$) and a second hollow section (55, 57) having a second internal cross-sectional area ($A_2$) being less than the first internal cross-sectional area ($A_1$); and the sensor arrangement (9, 25, 27, 39, 41, 43, 44, 45, 46, 47), is for measuring the difference between stagnation and static pressures ($P_{01}$, $P_{02}$, $P_1$, $P_2$) within the second hollow section (55, 57).

16 Claims, 13 Drawing Sheets

(56) References Cited

U.S. PATENT DOCUMENTS

| | | | | |
|---|---|---|---|---|
| 3,750,472 A * | 8/1973 | Ducousset | ............... | G01F 1/86 73/861.02 |
| 6,138,675 A * | 10/2000 | Berthon-Jones | ....... | A61B 5/087 128/204.23 |
| 6,463,810 B1 * | 10/2002 | Liu | ........................ | G01F 1/44 73/861 |
| 7,192,403 B2 * | 3/2007 | Russell | ............. | A61B 5/02007 600/485 |
| 2004/0168508 A1 | 9/2004 | Henderson et al. | | |
| 2009/0139348 A1 | 6/2009 | Speldrich | | |
| 2011/0125045 A1 * | 5/2011 | Scholz | ................... | A61B 5/087 600/538 |

FOREIGN PATENT DOCUMENTS

| | | | |
|---|---|---|---|
| ES | 2192441 A1 | 10/2003 | |
| GB | 196 134 A | 4/1923 | |
| GB | 2246865 A | 2/1992 | |
| JP | H01101972 A | 4/1989 | |
| JP | 2006162417 A | 6/2006 | |
| KR | 1020060016557 A | 2/2006 | |
| WO | 9718003 A1 | 5/1997 | |
| WO | WO-9718003 A1 * | 5/1997 | ............ A61B 5/087 |
| WO | 0167949 A1 | 9/2001 | |
| WO | 03089883 A1 | 10/2003 | |
| WO | 2004049940 A1 | 6/2004 | |

OTHER PUBLICATIONS

Aman Mahajan et al. "Continuous Monitoring of Dynamic Pulmonary Compliance Enables Detection of Endobronchial Intubation in Infants and Children" Anesthesia & Analgesia, Jul. 2007, vol. 105, No. 1, pp. 51-56, 2007 International Anesthesia Research Society.
Rennie, CE; Gouder, KA; Taylor, DJ; et al. Nasal Inspiratory Flow: At Rest and Sniffing. International Forum of Allergy & Rhinology, 2011; vol. 1:128-135.

* cited by examiner

FLOW METER

CROSS-REFERENCE TO RELATED APPLICATIONS

This patent application is a United States National Stage Patent Application of PCT/GB2015/054101, filed Dec. 21, 2015, which in turn claims the benefit of Great Britain Patent Application No. GB1500257.9, filed Jan. 8, 2015. The entire disclosures of the above patent applications are hereby incorporated herein by reference.

FIELD OF THE INVENTION

The present invention relates to a flow meter; certain embodiments of the present invention relate to a respirometer.

BACKGROUND OF THE INVENTION

There is a clinical need for accurate measurements of a person's oral and nasal respiration. These measurements are of value, for example, in modelling nasal air conditioning, odorant transport and drug delivery. Currently, techniques available to obtain time-accurate measurements of human respiration are limited, and may require complex hardware setups, necessitating clinical visits and considerable discomfort for patients. Alternative, non-intrusive measurement techniques, such as the use of nasal prongs, may be effective but necessarily cannot provide accurate measurements of flow rates.

A previous study ("Nasal inspiratory flow: at rest and sniffing", Rennie et al., International Forum of Allergy & Rhinology, Vol. 1, No. 2, March/April 2011, hereinafter referred to as "Rennie et al. (2011), and the content of which is incorporated herein by reference in its entirety) documents the use of a hotwire anemometry-based system to quantify the time-varying flow rate during inspiration at rest and in sniffing. This technique was adopted, as a high-precision measurement of the time-evolution of low volumetric flow rates was required, and no alternative measurement technique was available. However, by its very nature, hotwire anemometry is fundamentally inappropriate for this particular application, as it is temperature dependent; this can limit its accuracy, particularly for exhalation measurements which would be affected by a patient's body temperature.

It is, therefore, an object of embodiments of the present invention to seek to alleviate the above identified problems. It is however to be understood that the present invention is by no means limited to respirometry. Rather, the present invention seeks to provide an improved flow meter in general, or at least to provide a useful alternative to existing flow meters.

SUMMARY OF THE INVENTION

According to an aspect of the present invention, there is provided a flow meter comprising a sampling tube through which fluid may flow and a sensor arrangement,
  wherein the sampling tube comprises a first hollow section having a first internal cross-sectional area and a second hollow section having a second internal cross-sectional area being less than the first internal cross-sectional area; and
  the sensor arrangement is for measuring the difference between stagnation and static pressures within the second hollow section.

Preferably, the sensor arrangement comprises one or more stagnation pressure measurement ports located within the second hollow section.

Preferably, the sensor arrangement comprises two stagnation pressure measurement ports located within the second hollow section and facing in opposite directions.

Preferably, the two opposite-facing stagnation ports are embedded within a single cylindrical body.

Preferably, the single cylindrical body has hemispherically-shaped ends, coaxial with the sampling tube at the middle of the second hollow section.

Preferably, the single cylindrical body is supported by a strut through which the stagnation pressures are transferred to sensors.

Preferably, the flow meter further comprises a housing, and the sensors are located within the housing.

Preferably, the sensor arrangement comprises one or more static pressure measurement ports located adjacent to the one or more stagnation pressure measurement ports.

Preferably, the or each static pressure measurement port is located at the same longitudinal position within the sampling tube as the or each adjacent stagnation pressure measurement port.

Preferably, the internal profile of the sampling tube is longitudinally symmetric.

Preferably, the flow meter further comprises a housing to which the sampling tube is removably mounted.

Preferably, the sensor arrangement further comprises sensor circuitry located within the housing.

Preferably, the sensor circuitry comprises an electronic controller.

Preferably, the sensor circuitry comprises at least one differential pressure transducer.

Preferably, each of the one or more stagnation pressure measurement ports is in communication with the sensor circuitry via one or more channels formed integrally in a wall of the housing.

Preferably, each of the one or more stagnation pressure ports is provided at an end of a respective stagnation pressure measurement tube integrally formed with the housing.

Preferably, each of the one or more stagnation pressure measurement tubes extends upwardly from an exterior surface of the wall of the housing and the sensor circuitry is located adjacent an interior surface of the wall, directly underneath the one or more stagnation pressure measurement tubes.

Preferably, the flow meter comprises a respirometer and the internal geometry of the sampling tube minimises pressure head loss to the limit of the subject's breathing sensitivity while maximizing the cross-sectional uniformity of the flow and minimizing the probability of flow separation from the walls.

Preferably, the first cross-sectional area is about double the second cross-sectional area.

Preferably, the first hollow section is linked to the second hollow section by a contoured section.

Preferably, the sensor arrangement further comprises a temperature sensor for measuring temperature within the second hollow section.

Preferably, the internal dimensions of the sampling tube may be altered.

Preferably, the sampling tube is operable to change its internal dimensions in use, in order to adjust its sensitivity in response to signals received by the flow meter.

Preferably, the sampling tube is provided with at least one interior surface defining at least part of an interior profile of the sampling tube and which is movable between at least a first condition and a second condition to alter the interior profile of the sampling tube.

Preferably, the at least one interior surface comprises at least part of a surface of the second hollow section.

Preferably, the flow meter further comprises a pressure transducer adjacent to the sampling tube for direct measurement of absolute pressures within the sampling tube.

Preferably, the flow meter comprises a respirometer.

Preferably, the flow meter comprises a high-sensitivity, low-range flow meter.

Preferably, the flow meter is arranged to sample stagnation pressure directly within a constriction within the sampling tube.

Preferably, the flow meter is arranged to sample stagnation pressure at only one location within the sampling tube.

Preferably, the flow meter is arranged to sample static pressure at the same streamwise location as the stagnation pressure.

Preferably, the flow meter has a fast response.

Preferably, the flow meter is arranged to make between 1,000 and 3,000 pressure measurements per second.

Preferably, the flow meter is arranged to make between 1,500 and 2,500 pressure measurements per second.

Preferably, the flow meter is arranged to make about 2,000 pressure measurements per second.

Preferably, the flow meter is arranged to make 2,000 pressure measurements per second.

Preferably, the flow meter is bidirectional.

Preferably, the flow meter further comprises an accelerometer, for measurement of a subject's breathing movements and/or activity.

Preferably, the accelerometer comprises an acceleration sensor for attachment to a subject's chest.

Preferably, the flow meter further comprises a pulse oximeter, for usage in measuring systemic arterial blood $O_2$ saturation.

Preferably, the flow meter further comprises a capnometer sensor, for usage in the measurement of carbon dioxide partial pressure ($PCO_2$) in a subject's expired air.

Preferably, the flow meter further comprises local memory to store measurement results for later download to an external device.

Preferably, the flow meter is arranged to transmit measurements wirelessly Preferably, the flow meter is provided with its own internal power source.

Preferably, the flow meter is provided with a humidity meter for providing additional diagnostic data or to allow further improvement of sensitivity and accuracy by correcting velocity estimates for humidity in the fluid.

Preferably, the flow meter further comprises a pressure sensor to measure the absolute pressure within the sampling tube.

Preferably, the flow meter is provided with a variable-geometry constriction.

Preferably, the flow meter is provided with a powered iris or other movable arrangement within its interior, to allow the internal profile of the sampling tube to be adjusted dynamically in use, for example under control of a microcontroller.

Preferably, the flow meter is operable to alter dimensions of a sampling section of the sampling tube relative to the remainder of the sampling tube.

Preferably, the flow meter further comprises a pressure sensor to directly measure the head loss, allowing the user to specify either the desired accuracy or maximum allowable interference.

Preferably, the flow meter is provided with interchangeable sensor elements.

According to another aspect of the present invention, there is provided a flow meter comprising a sampling tube through which fluid may flow and a sensor arrangement for measuring pressures within the sampling tube,
wherein the sensor arrangement comprises two stagnation tubes located within the sampling tube and facing in opposite directions.

Preferably, the internal profile of the sampling tube is longitudinally symmetric.

According to a further aspect of the present invention, there is provided a flow meter system comprising:
a flow meter as described herein, wherein the sampling tube comprises a first sampling tube of the flow meter system; and
a second sampling tube through which a fluid may flow, interchangeable with the first sampling tube.

Preferably, the first and second sampling tubes present different internal profiles.

According to a yet further aspect of the present invention, there is provided a fluid flow measurement method, comprising obtaining pressure measurements relating to the pressure of fluid within a sampling tube of a flow meter as described herein or a flow meter system as described herein, when fluid flows through the sampling tube.

Preferably, the method further comprises measuring the temperature of a fluid within the sampling tube.

Preferably, the method further comprises determining a volumetric flow rate of fluid flow within the sampling tube based at least in part upon the pressure and/or temperature measurements.

Preferably, the method further comprises determining a mass flow rate of fluid within the sampling tube based at least in part upon the pressure and/or temperature measurements.

According to another aspect of the present invention, there is provided a computer-readable carrier medium carrying computer readable instructions for performing a fluid flow measurement method as described herein.

According to a still further aspect of the present invention, there is provided a computer programmed to perform a fluid flow measurement method as described herein.

DETAILED DESCRIPTION

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein and vice versa. Further, it is to be understood that although certain of the following embodiments are described in relation to respirometry, the present invention is by no means limited to respirometers and respirometry; rather, the present invention encompasses flow meters generally and the features described in relation to respirometer embodiments may be applied to flow meters for other applications according to embodiments of the present invention.

In order that the present invention may be more readily understood, embodiments thereof will now be described, by way of example only, with reference to the accompanying drawings, of which:

The inventors have appreciated that measuring air velocity through the relationship between velocity and pressure is beneficial to the field of respirometry, as it may be used to provide a robust, reliable and temperature-independent/weakly dependent method for determining air velocity. The most sensitive measure is that of the static-to-stagnation pressure difference; this is the concept by which conventional Pitot-type velocity probes can infer local fluid velocity. However, these can provide only a local measurement. A first embodiment of the present embodiment therefore imposes a prescribed velocity profile to allow total volumetric flow rates to be determined. In the first embodiment, this is achieved by conditioning the incoming fluid flow through a development length of tube and a constriction, and then measuring the difference between the local static and stagnation pressures independently. Bi-directionality is achieved by using two opposite-facing total pressure probes (one for inhalation, one for exhalation) in the core flow. The local temperature is also sampled. The volumetric flow rate is then inferred from these signals, such that the present embodiment provides a high-sensitivity bi-directional volumetric flow meter for particular application in medical diagnostics, which is arranged to measure the flow rate of air with minimal intrusiveness during typical human respiration as a function of time.

Figure 1:
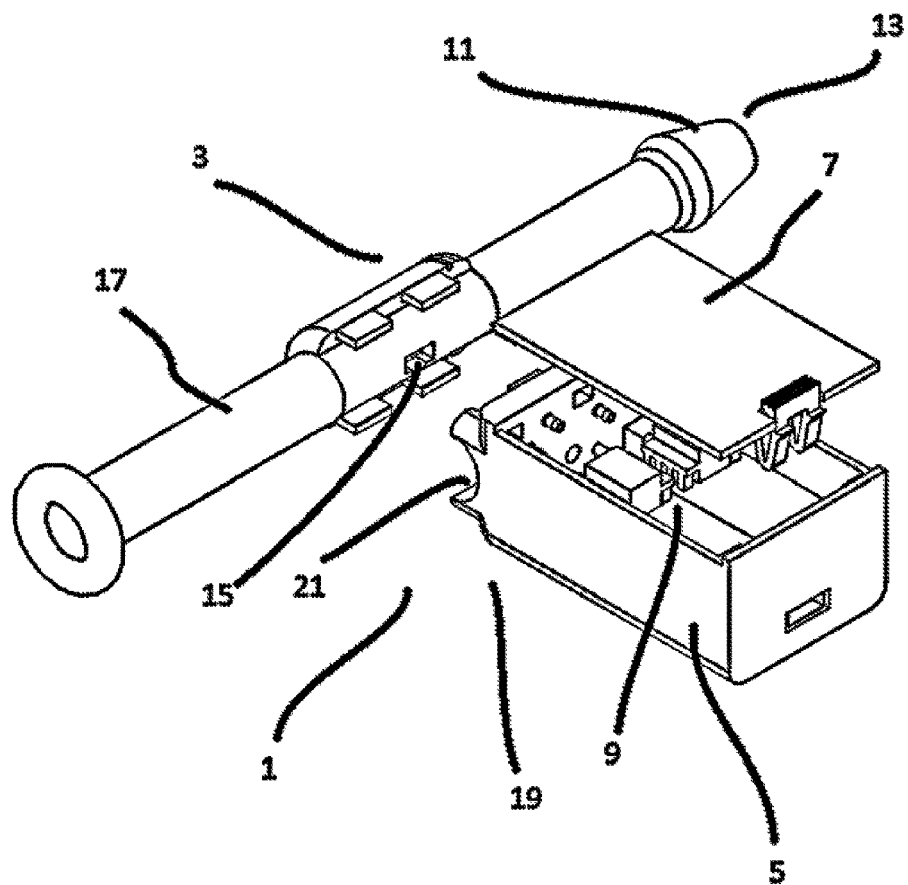
FIG. 1 is an exploded perspective view of a respirometer according to a first embodiment of the present invention.

FIG. 1 is an exploded view of a flow meter 1 according to the first embodiment of the present invention, and which generally comprises a sampling tube 3, a housing 5, a housing cover 7 and electronic and sensor circuitry 9 contained within the housing 5.

The flow meter of the present embodiment is intended to be used as a respirometer, and accordingly is described in the following as a respirometer. It is however to be understood that this is not limiting, and that features and advantages described in the following may equally be applied to a flow meter according to an embodiment of the present invention, applicable to other fields beyond respirometry.

Figure 2:
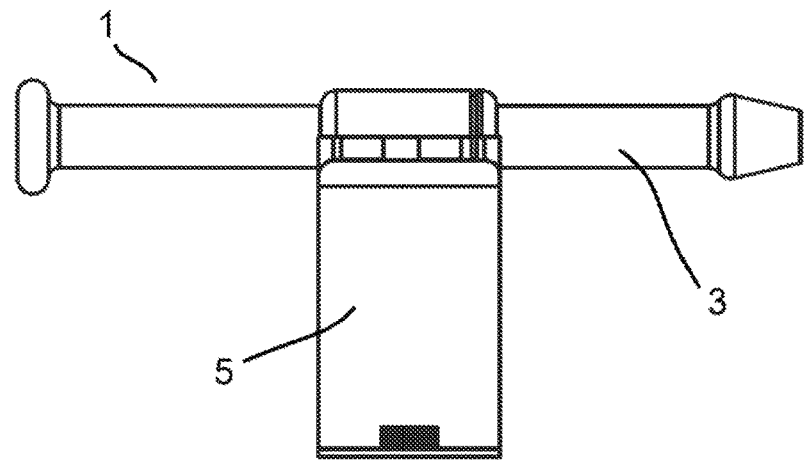
FIG. 2 shows the respirometer of FIG. 1 in an assembled condition.

The sampling tube 3 is removably mounted to the housing 5 in a "snap-fit" fashion to form the assembled respirometer 1 shown in FIG. 2, and is intended to be disposable for purposes of infection control. The sampling tube 3 has a frustoconical end piece 11 at a first end 13 thereof to facilitate sealing with a subject's nostril during nasal use of the respirometer 1. An aperture 15 formed in the sidewall 17 of the sampling tube 3 leads to a sampling section 18 (see FIG. 3) within the hollow interior of the sampling tube 3, described in greater detail hereinafter.

The housing 5 of the present embodiment forms the body of the device which may readily be held by a subject breathing through the sampling tube 3; the removable "clip-on" housing cover 7 is used to protect the sensor circuitry 9 contained within the housing 5, and to conveniently provide a holding surface, during use of the respirometer 1.

Figure 3:
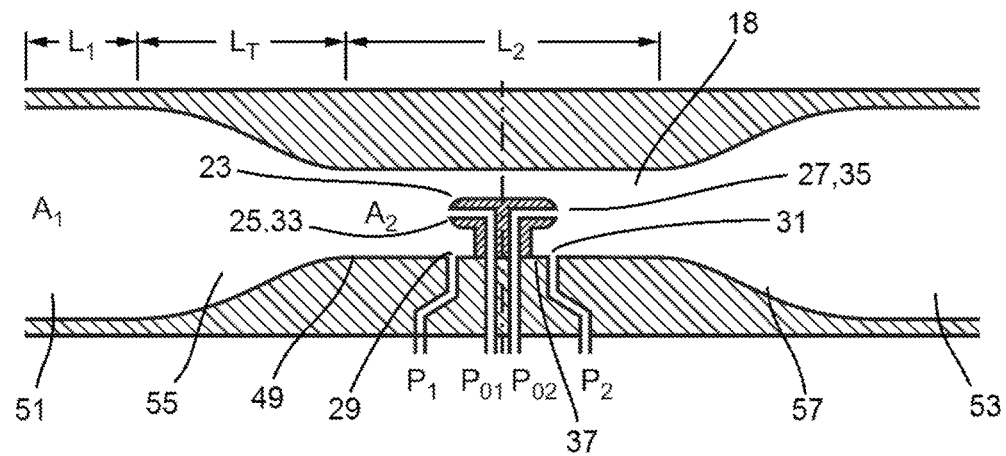
FIG. 3 is a schematic cross-sectional view through a portion of the assembled respirometer of FIG. 2.

An upper, tube-receiving end 19 of the housing 5 is provided with a saddle portion 21 for receiving a central section of the sampling tube 3. Referring to FIG. 3, a probe head 23 is further provided on the tube-receiving end 19 of the housing 5 which incorporates a pair of simple stagnation probes 25, 27 of minimal diameter facing in opposing directions and a pair of static pressure ports 29, 31. In the present embodiment, the stagnation probes 25, 27 each have an outer diameter of 1.2 mm and an inner diameter of 0.6 mm; the tips of the stagnation probes are provided with hemispherical end-caps in which the stagnation ports 25, 27 are located. Each static pressure port 29, 31 is located to coincide at the same longitudinal position within the sampling tube 3 as the inlet 33, 35 of a respective one of the stagnation probes 25, 27, to enable dynamic pressure measurements to be made of the fluid within the sampling tube 3. For temperature measurements to be taken, the probe head 23 is further provided with a temperature sensor 37 located at the base of the probe head 23, flush with the sampling tube wall. The probe head 23 is arranged to protrude through the aperture 15 in the sidewall 17 when the sampling tube 3 is mounted to the housing 5, to enable the stagnation probes 25, 27 to adopt a radially-central position and the temperature sensor 37 to adopt a wall-flush position within the sampling section 18 of the sampling tube 3, in the assembled respirometer 1.

In the present embodiment, the housing 5 is constructed from a UV cured polyurethane-acrylic polymer, using a selective-curing rapid prototyping machine. This readily enables the housing 5 to be directly and integrally formed with the stagnation probes 25, 27 and static pressure ports 29, 31, with no further/discrete tubing etc. being required. Other methods may however be used to manufacture the housing 5, for example injection-moulding. The sampling tube 3 may for example be readily and inexpensively manufactured by an injection moulding process.

Figure 4:
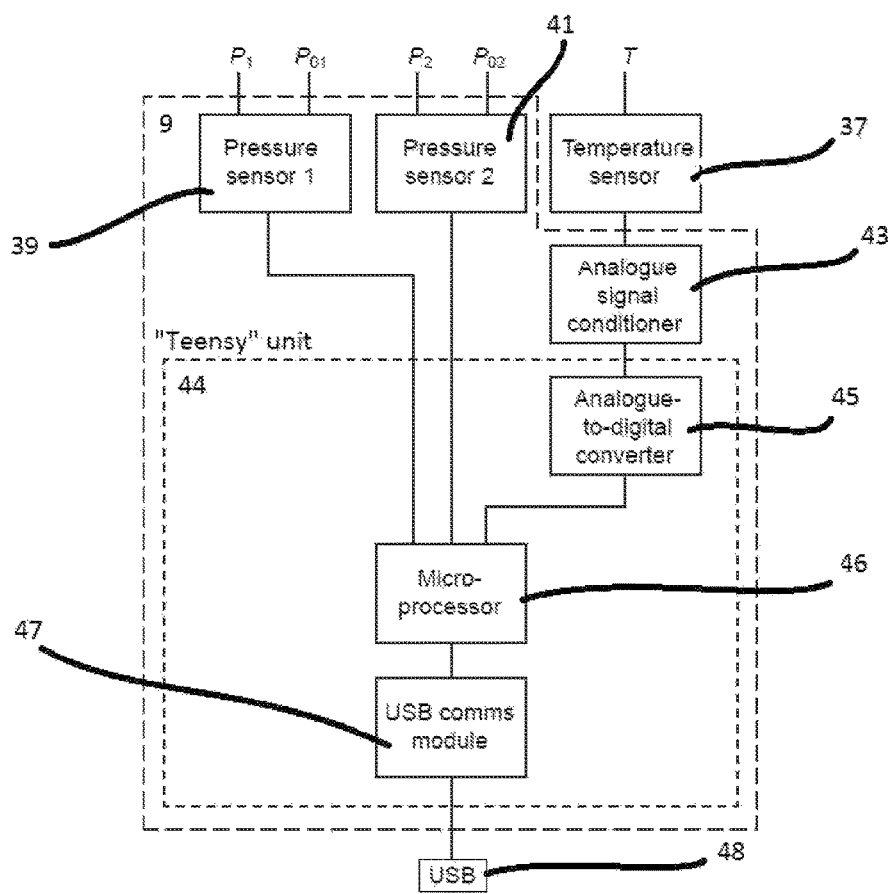
FIG. 4 is a schematic view of electronic systems of the respirometer of the first embodiment.

The sensor circuitry 9 is shown schematically in FIG. 4 and comprises a pair of low-range digital differential pressure transducers 39, 41, an analogue signal conditioner 43, and a microcontroller unit 44 (which in the present embodiment includes an analogue-to digital converter 45, a microprocessor 46, a USB communications module 47, a power conditioning unit (not shown) and an output module (not shown)). Each of the pair of pressure transducers 39, 41 takes two inputs—a stagnation pressure input, from a respective one of the two stagnation probes, and a static pressure input, from the static pressure port adjacent the stagnation probe providing the stagnation pressure input for that pressure transducer, and outputs differential pressure data to the microcontroller unit 44 based upon these inputs. Similarly, the temperature sensor 37 outputs temperature data measurements, via the analogue signal conditioner 43, to the microcontroller unit 44. The microcontroller unit 44 manages/controls the communications with the digital pressure transducers and temperature sensor 37 and streams the dynamic pressure data and fluid temperature data out of the respirometer 1 via the USB communications module 47 e.g. to a computer, using standard USB protocols. Software drivers and a computer user interface are also provided according to a further aspect of the present intention, to allow management and display of the pressure and temperature data.

Figure 5A:
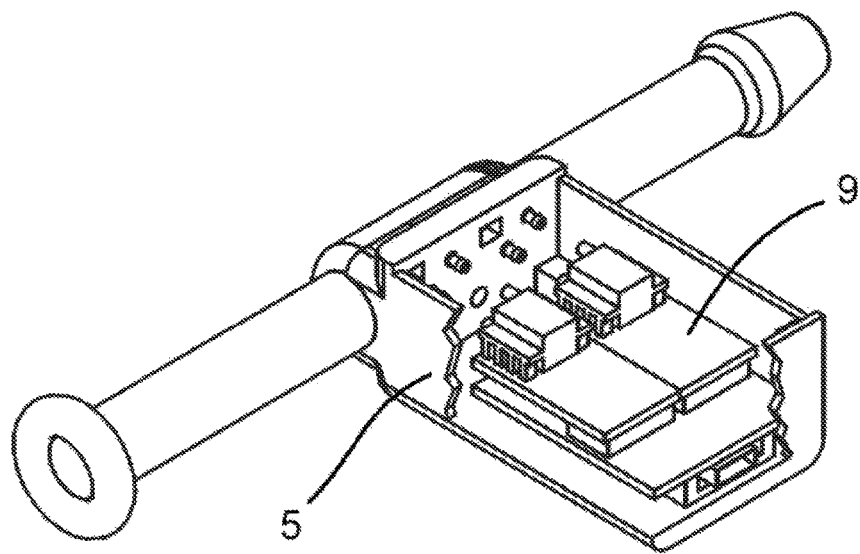
FIG. 5A shows the respirometer of FIG. 1 with sensor circuitry indicated.
Figure 5B:
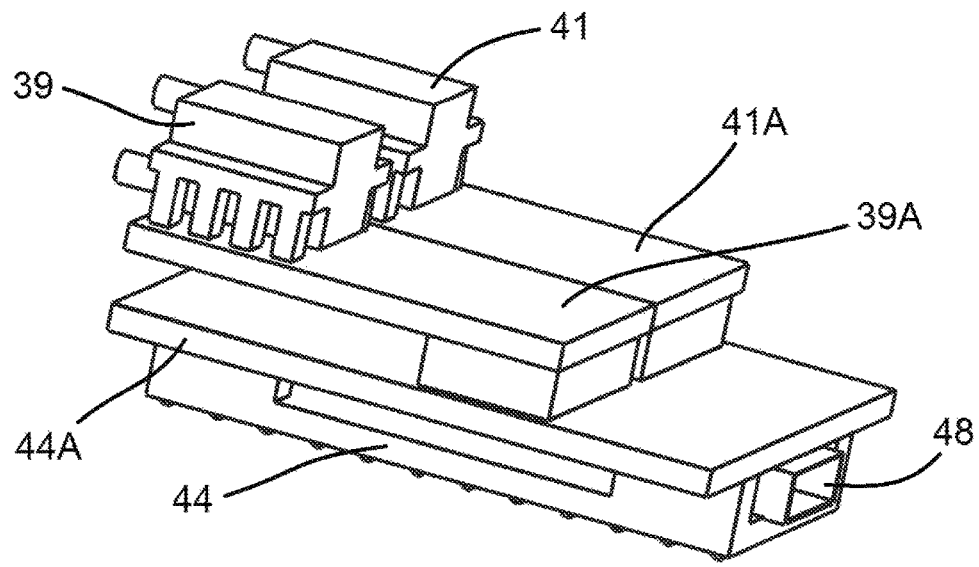
FIG. 5B shows the sensor circuitry of FIG. 5A in greater detail.

FIG. 5A highlights the sensor circuitry 9 within the housing 5 and FIG. 5B shows the circuitry 9 in greater detail. Tubing connecting the housing 5 to the pressure transducers 39, 41 has been omitted for clarity from these Figures (as well as from FIG. 1); the cover 7 has also been omitted, and the housing 5 shown in cutaway, for clarity and illustrative purposes in FIG. 5A. As shown in FIG. 5B, the pressure transducers 39, 41 are mounted to transducer cards 39A, 41A, which are in turn mounted to sockets provided on a signal distributor card 44A. The signal distributor card 44A further includes a thermistor driver (not shown) and re-arranges pin order to be directly compatible with the microcontroller unit 44, to which the signal distributor card 44A is mounted; a USB port 48 of the USB communications module 47 is located at a distal end of the microcontroller unit 44.

FIG. 3 shows the sampling tube 3 in cross-section.

The hollow interior of the sampling tube 3 is longitudinally symmetric to provide bidirectional sensitivity (for monitoring both inhalation and exhalation), and is profiled to present a constriction (generally shown at 49 in FIG. 3) defining the sampling section 18 which is of reduced cross-sectional area in a plane substantially perpendicular (i.e. between about 85 degrees and 95 degrees), and preferably perpendicular, to the direction of fluid flow, and is located at a central region of the sampling tube 3. The sampling section 18 is in communication with first and second development sections 51, 53, such that fluid may flow from one to the other, via first and second transition sections 55, 57.

On inhalation, fluid (air in normal usage) enters the first development section 51 of circular cross sectional area $A_1$ and length $L_1$, within which the flow can achieve a reasonably uniform, axisymmetric distribution. The first transition section 55, of length $L_T$, acts as a constriction through which the flow is accelerated to enter the sampling section 18 of reduced circular cross sectional area $A_2$ and total length $L_2$; this will reduce the thickness of the boundary layers while damping any turbulence remaining in the fluid.

The fluid then encounters a first and then a second of the two stagnation probes 25, 27 within the sampling section 18. The first stagnation probe 25 encountered is that with its inlet facing directly into the flow (and away from the subject inhaling through the sampling tube 3). The first stagnation probe 25 which yields the stagnation pressure $P_{O1}$ and the static port 29 adjacent the first stagnation probe 25 yields the static pressure $P_1$, from which the dynamic pressure of the flow is determined. The second stagnation probe encountered has its inlet facing away from the flow. The second stagnation probe yields a stagnation pressure $P_{O2}$ and its adjacent static port 31 yields a static pressure $P_2$, from which a further dynamic pressure measurement, lower than that determined using the first stagnation probe 25, is determined. This "false" reading is simply discarded. The fluid also encounters the temperature sensor 37, yielding the temperature measurement T. The fluid then exits the sampling section 18 and is expanded through the second transition section 57 (of identical length $L_T$ and geometry as the first transition section 55, but reversed so that the cross-sectional area increases in the direction of flow), which acts as a wide-angle diffuser, via which the fluid reaches the second development section 53 (of the same circular cross sectional area $A_1$ and length $L_1$ as the first development section 51) to exit the sampling tube 3.

On exhalation, the situation is simply reversed, with the fluid (exhaled air) entering the sampling tube 3 via the second development section 53 and the dynamic pressure measurement being determined using the reverse-facing stagnation probe 27 (which will be facing directly into the exhaled fluid flow) and its adjacent static pressure port 31.

In order to drive the flow through the sampling tube 3, some pressure head will necessarily be required to be generated by a subject. The present inventors have appreciated that the faster the flow is driven through the constriction 49, the more sensitive the measurements but the more pressure head will be lost; equally, increasing the length of the development section will improve flow uniformity but increase head loss. A loss of pressure head will cause the respirometer to affect the quantity being measured, as a subject will need to exert more effort in breathing through the respirometer 1 than they would do when breathing normally. The sampling tube 3 of the present embodiment has therefore been designed to provide sufficient sensitivity for useful measurement while incurring imperceptible head loss. The following describes the analytical development employed by the inventors in designing the sampling tube 3 of the present embodiment.

Analytical Development

A. Volumetric Flow Rate

For the purposes of the present invention, we assume that the pattern of human respiration may be described as:

$$V(t) = V_0 + V_\alpha F(t), \quad (1)$$

where $V(t)$ is the volume contained within the human lungs at any given time, $V_\alpha$ is the tidal volume of air inhaled and exhaled, $V_0$ is the volume of air stagnating within the lungs, and $F(t)$ is some unknown periodic function of time (of frequency f) such that $-1 \leq F \leq 1$. The volumetric flow rate $\dot{V}$ of air through respiration is then given by differentiating equation (1) as $$\dot{V} = V_\alpha \frac{dF}{dt}. \quad (2)$$

If, as a first approximation, $\dot{V}$ is taken as being approximately constant during each of the inhalation and exhalation phases (which appears to be a reasonable assumption—see Rennie et al. (2011)), then $$\dot{V} \approx 2 f V_\alpha. \quad (3)$$

B. Flow Development

In developing (smooth wall) pipe flow, the centreline velocity U varies with the development length x from the pipe entrance as $$\frac{U(x)}{U_0} = 1 + 1.72 \left( \frac{vx}{R^2 U_0} \right)^{1/2}; \quad (4)$$

where $U_0$ is the uniform inlet velocity, $v$ is the kinematic viscosity, and R is the pipe radius (see Shlichting, H., Boundary Layer Theory, 4th Ed., McGraw-Hill, 1960, hereinafter "Shlichting, 1960") the content of which is incorporated herein by reference in its entirety). Alternatively, for the case of a circular pipe, equation (4) may be expressed in terms of the volumetric flow rate (using equation (3)) as $$\frac{U(x)}{U_0} = 1 + 1.72 \left( \frac{\pi v x}{2 f V_\alpha} \right)^{1/2}. \quad (5)$$

Equation (5) then provides a measure of the uncertainty in volumetric flow measurement incurred as a consequence of the developing boundary layers in the internal pipe flow.

C. Head Loss

There is no simple analytical model for the head loss through a pipe with developing flow. However, an exact solution to the Navier-Stokes equations for the case of fully-developed laminar pipe flow yields, $$U_0 = -\frac{R^2}{8\mu} \frac{dP}{dx}, \quad (6)$$

where $\mu = \rho v$ is the absolute fluid viscosity, and $\rho$ is the fluid density. Since the head loss in fully-developed flow is always greater than that in developing flow, equation (6) provides a useful upper limit for the present case. Substituting equation (3) and assuming constant geometry, $$\Delta P = \frac{16}{\pi} \mu f V_\alpha R^{-4} L_0, \quad (7)$$

where $\Delta P$ represents the pressure required to drive the flow, and $L_0$ is the length of the tube. The minor head losses caused by the contraction and expansion will typically be small by comparison.

D. Data Reduction

The interpretation of data from Pitot-static probes is already well-established; see, for example, the detailed description in Tropea, C., Yarin, A. L., and Foss, J. F., E., Springer Handbook of Experimental Fluid Mechanics (Springer, 2007), the content of which is incorporated herein by reference in its entirety. Assuming incompressible flow, the velocity U of a fluid is related to the pressure difference as $$U = \left( \frac{2}{\rho} (P_0 - P) \right)^{1/2}. \quad (8)$$

However, for the case of gases the fluid density cannot be sampled directly. Instead, the density may be inferred from ambient pressure and the fluid temperature T, as $$\rho = \frac{P}{\Re T}, \quad (9)$$

where $\Re$ is the specific gas constant of the gas. Substituting equation (9) into equation (8), $$U = \left( 2\Re T \left( \frac{P_0}{P} - 1 \right) \right)^{1/2}. \quad (10)$$

However, this will require the measurement of two independent pressures per velocity channel. Instead, by assuming that $P \sim P_a$ (where $P_a$ is the standard atmospheric pressure), equation (10) may be expressed instead as $$U \approx \left( \frac{2\Re T}{P_a} (P_0 - P) \right)^{1/2}, \quad (11)$$

thereby allowing the velocity to be inferred from a single differential pressure measurement and a single local temperature measurement. Hence, making this assumption (that $P \sim P_a$) allows a simplified flow meter to be produced. In further embodiments, however, a third, absolute pressure sensor may be included to measure the full (absolute) thermodynamic state of the fluid in the tube. Note that changes in fluid density during normal breathing will be small. For the case of a bi-directional probe assembly formed of two reverse-facing stagnation tubes, as in the present embodiment, the velocity direction may be inferred by simply ignoring the lesser of the two pressures recorded.

Alternatively, the pressure difference $P_0 - P$ may be related to the breathing cycle by combining equation (3) with equations (11) and (9), as $$P_0 - P = \frac{2P_a f^2 V_a^2}{\pi^2 RTR^4}. \quad (12)$$

where again it has been assumed that $P \sim P_a$.

The nonlinearity in equation (11) does, however, give rise to a nonlinear precision; if the pressure difference $P_0-P$ is only known to within an error margin $\epsilon_P$, then the uncertainty in the velocity $\epsilon_U$ will be given by, $$\epsilon_P = \frac{\rho}{2}(\epsilon_U^2 + 2U\epsilon_U). \quad (13)$$

In the following, the design of the respirometer 1 of the present embodiment is set out in greater detail.

Respirometer Design

A. Geometry

In designing the present embodiment, the inventors assumed a typical tidal breathing volume of $V_a \sim 0.5$ L, together with a frequency of 0.2 to 0.33 Hz, to determine the dimensions shown in FIG. 3 based on the requirements described above. For practical purposes, it is preferable that a total sampling tube length $2(L_1+L_T)+L_2$ of 150 mm is imposed, as is a sampling tube entrance radius $R_1=5$ mm (corresponding to a maximum area $A_1=79$ mm$^2$). For the purposes of flow conditioning, the present inventors have appreciated that design rules established in a wind tunnel study (Mehta, R. D. and Bradshaw, P., "Design rules for small low-speed wind tunnels," Aeronaut. J. 718, 443-449, 1979, the contents of which are hereby incorporated by reference in their entirety) may beneficially be applied and hence a constriction ratio of $A_1/A_2 \sim 2$ is desired, and a maximum diffuser wall angle of 10° is preferable. These requirements result in a constriction radius $R_2 \sim 3.55$ mm and nozzle/diffuser length $L_T \sim 8.3$ mm. A minimum constriction length $L_2$ is desired, although this must be sufficiently long to accommodate the sampling ports; a length $L_T=10$ mm is therefore selected in the present embodiment, resulting in a development length $L_1 \sim 61.7$ mm.

The net pressure head loss incurred as a consequence of this geometry will then be given by equation (7), as $$\Delta P = \frac{16}{\pi} \mu f V_a (2R_1^{-4} L_1 + R_2^{-4} L_2), \quad (14)$$

yielding a dimensional result of at most ~4 Pa, which is at the threshold of sensation for the human body (equivalent to the additional pressure applied to the chest cavity when attempting to breathe air at atmospheric pressure while immersed in water to a depth of 0.4 mm). Alternatively, if the human breathing passages are assumed to have an average diameter of 10 mm, the resultant pressure head loss would be approximately 24 Pa/m.

B. Selection of Pressure Transducer

An appropriate pressure transducer for the present embodiment was selected using approximations of the respiration rate. From equation (12), a breathing volume and frequency of 0.5 L and 0.2 Hz, respectively, result in a minimum full-scale pressure difference $P_0-P \sim 15$ Pa, assuming standard atmospheric conditions. A suitable, cost-efficient product for this pressure range is the Honeywell HSC-series of surface mount (SMT) differential pressure transducers. These are temperature-compensated, with integrated analogue-to-digital converters, a full-scale range of 250 Pa and 14-bit sensitivity (corresponding to a precision of 0.015 Pa). From equations (13) and (8), then, the sensitivity in velocity is $0.16 \leq \epsilon_U \leq 6.2 \times 10^{-4}$ m/s.

In the present embodiment, the pressure transducers 39, 41 are mounted on printed circuit cards and the microcontroller 45 comprises a "Teensy" unit; in the present embodiment, these components are selected to provide a very high sampling rate e.g. 2,000 measurements per second. Further, the distance between the stagnation probes 25, 27 and the pressure transducers 39, 41 is minimised as far as possible, in particular by locating the pressure transducers 39, 41 within the housing 5 directly underneath the stagnation probes 25, 27; this minimising of distance may be beneficial in increasing sensitivity and sampling rate.

Use of the present embodiment will now be described.

Unit Preparation and Installation

An operator attaches a new sampling tube 3 onto the respirometer housing 5. The sampling tube 3 can only be installed in one orientation in the present embodiment; to facilitate ready identification of the correct orientation, a groove is provided running around the sampling tube 3 which matches a similar groove in the housing 5 when the sampling tube 3 is oriented correctly.

The operator then connects the respirometer 1 to a computer using a suitable USB cable, having pre-installed suitable software and drivers (which are provided according to an embodiment of a further aspect of the present invention) onto the computer e.g. from a USB key, which according to an embodiment may for example be supplied as part of a kit with the respirometer 1; instructions for installing the software may also be included on the USB key. In the present embodiment, the USB link between the respirometer 1 and computer is used both for data transmission and to power the respirometer 1. The software may be arranged to present a graphical user-interface "dashboard" on the computer giving an indication (e.g. by way of an indicator turning green) of successful installation of the drivers and communication with the respirometer 1, and may invite the operator to choose a file path to save the data, to be entered into an appropriate field.

Using the Respirometer

With the respirometer 1 held steady and in the orientation in which it will be used, an "auto-zero" button is clicked on the software dashboard, and a prescribed period e.g. 10 seconds is allowed to pass before any further movement of the respirometer to allow auto-calibration to complete. For further control of the respirometer 1, various sample rates (e.g. up to 2 kHz in the present embodiment) can be chosen, the auto-zero time can be varied, and comments can be entered per recording (i.e. per file). The file write interval and precision may be specified by the user. The respirometer 1 is then ready for use.

The frustoconical end piece 11 is inserted into the subject's nostril or mouth and the subject breathes as normal. The dynamic pressure and temperature measurements determined by the respirometer 1 for both inhalation and exhalation of the subject are output to the computer (as detailed above) and recorded. The computer software may be used to produce further data based upon these measurements e.g. volumetric flow rate, or, using also the temperature measurements, the mass flow rate of fluid within the sampling tube 3.

Once sufficient measurements have been made, recording is stopped via the software dashboard, and the respirometer 1 is disconnected from the computer by removing the USB cable. The sampling tube 3 is then removed and discarded, and the housing 5 is sterilised for further use.

According to a further aspect of the present invention, the present embodiment may be supplied as a respirometer system, comprising the respirometer 1 and a plurality of sampling tubes 3 to allow the ready replacement of a used sampling tube.

Yet further, the respirometer system may comprise sampling tubes 3 of differing internal or external profile. In particular, the sensitivity of the respirometer 1 of the present embodiment is inversely proportional to the cross-sectional area $A_2$ of the sampling section 18. Hence, a sampling tube 3 having a sampling section 18 of increased cross-sectional area $A_2$ will be less sensitive. However, such a sampling tube 3 would present less back-pressure resistance to a subject, potentially rendering it more suitable for subjects having reduced lung strength e.g. in paediatrics, and also means that the respirometer 1 would be able to make measurements across a greater range of fluid flow velocity. Hence, the respirometer system may provide a plurality of different sampling tubes 3 of differing internal profile (e.g. internal dimensions and/or geometry) for use in different circumstances, with different subject types, etc.

Although it is envisaged that the sampling tube 3 would be disposable e.g. after a single instance of usage, the sampling tube 3 may alternatively be sterilized for further usage e.g. by immersion in isopropyl or denatured alcohol.

The present embodiment may also be modified; for example:

- It may include an accelerometer, for measurement of a subject's breathing movements/activity. This may for example be provided by way of a suitable acceleration sensor glued to the subject's chest and wired to the respirometer 1 assembly;
- It may include a pulse oximeter, for usage in measuring systemic (finger) arterial blood O2 saturation; this may for example be provided using a suitable pulse oximeter device cabled or wirelessly connected to the respirometer 1 unit;
- It may include a capnometer sensor, for usage in the measurement of carbon dioxide partial pressure ($PCO_2$) in expired air;
- It may for example be provided with local memory (e.g. SD card) to store measurement results for later download to an external device. Alternatively, the respirometer 1 may be arranged to transmit the measurements wirelessly, rather than via the USB port 48 and cable. Either option will eliminate the need for a direct wired connection to a computer during measurement; the respirometer may be provided with its own internal power source e.g. battery pack in such applications;
- It may for example be provided with a humidity meter which could provide additional diagnostic data (hydration levels, gas exchange rates), or allow further improvement of sensitivity and accuracy by correcting the velocity estimates for humidity in the air;
- It may for example be provided with a third pressure sensor to measure the absolute pressure within the sampling tube, to avoid relying on the assumption that local pressure is the same as atmospheric;
- It may be provided with a variable-geometry constriction. For example, the respirometer may be provided with a powered iris or other movable arrangement within its interior, to allow the internal profile of the sampling tube to be adjusted dynamically in use, for example in accordance with control signals sent by the microprocessor 46 via the output module of the microcontroller unit 44. In particular, by altering the dimensions of sampling section 18 relative to the remainder of the sampling tube (in particular, by altering the size of the sampling section 18 and/or the size of the reminder of the interior of the sampling tube) the sensitivity of the respirometer 1 may be dynamically adjusted depending on the measurements, driven by the microcontroller 46. This would significantly extend the range of use of the respirometer 1. This may extend to permitting the respirometer 1 to operate as a null-reading system for even greater sensitivity;
- It may be provided with a fourth pressure sensor to directly measure the head loss, allowing the user to specify either the desired accuracy or maximum allowable interference;
- It may be provided with interchangeable sensor elements, to offer a wider product family (in terms of sensitivity versus full-scale range).

Sample Demonstration Results

Figure 6:
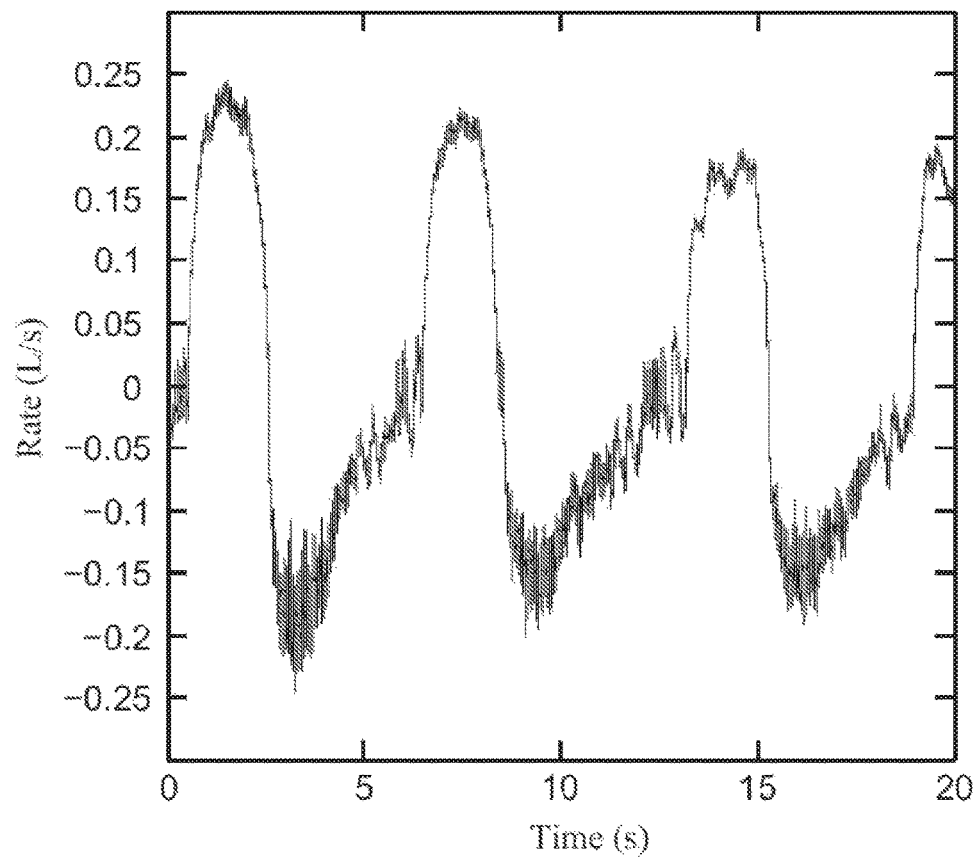
FIG. 6 is a graph showing typical results recorded using an instance of a respirometer manufactured according to the first embodiment.

Several cycles of normal breathing were recorded, using an instance of a respirometer manufactured according to the present embodiment, collected from a volunteer in a relaxed, seated position. FIG. 6 shows some typical results, which qualitatively agree with those obtained in the above-mentioned study by Rennie et al. (2011).

A manufactured instance of the present embodiment was tested, and the following operating parameters were derived:

| Quantity | Min | Max | Units |
| --- | --- | --- | --- |
| Flow rate | −0.8 | 0.8 | L/s |
| Flow temperature | 10 | 50 | ° C. |
| Ambient temperature | −20 | 85 | ° C. |
| Humidity | 0 | 95 | % relative |
| Ambient pressure | 0.5 | 1.5 | atm. |
| Bandwidth | — | 2 | kHz |
| Sampling time | — | — | (unlimited) |
| Component accuracy | 0.5% | — | Full scale |

A comparison of physiological breathing parameters was performed by comparing data acquisition capabilities of a manufactured instance of the first embodiment to characteristic values of the target quantities being measured. The physiologic quantities are characteristic of a healthy adult.

| Physiologic Quantity | System Performance | | Comment |
| --- | --- | --- | --- |
| Breathing Frequency: [12; 20] bpm = [0.2; 0.33] Hz | Number of Sample Points per Breath: ((60 × 100 ms/min)/([12; 20] breaths/min)) × (1/ (0.5 ms/sample)) = [600; 1000] | Very high temporal resolution | Acquisition of very detailed respiratory profiles |
| Peak Inspiratory Flow Rate (rest): 350 mL/s = 21,000 SCCM = 21 SLPM | Sensitivity: (1.46/21,000) × 100 = 0.007% of peak flow rate | Very high airflow rate resolution | Acquisition of very detailed respiratory profiles |

As will be appreciated, the present application discloses an embodiment of a Fast Respirometer being a compact, portable device capable of measuring volumetric respiration/breathing rates as a function of time. The unit is intended for clinical use, in the diagnosis, characterisation and management of respiratory diseases and disorders. In particular, the embodiment relates to a high-sensitivity, bi-directional time-accurate volumetric flow meter for use in medical and clinical applications e.g. in the diagnosis and management of respiratory conditions.

The fast respirometer unit directs air through a longitudinally-symmetric sampling chamber, and measures the local air speed using a bi-directional stagnation-static pressure probe. The geometry of the sampling chamber then allows the volumetric flow rate to be inferred. The unit also measures the temperature of the air, which allows the mass flow rate to be inferred.

Pressures are digitized using a pair of low-range digital pressure transducers, and output to a computer through a micro-USB port 48 via an internal microprocessor 46. The internal microprocessor 46 may also be programmed to convert the signals to any desired format.

Features of the present embodiment may include:

High-frequency data acquisition of up to 2 kHz for both pressure and temperature data (e.g. user specified), or equivalently minimum time between sampled of 0.5 ms;

Bi-directional pressure/temperature data acquisition, allowing for monitoring of both inspiratory and expiratory profiles;

Static-to-stagnation pressure differential measurement by stagnation pressure and static pressure ports;

Net head loss of approx. 4 Pa, at limit of human breathing sensitivity;

Temperature measurement by muRata NTC thermistor with high precision to e.g. 0.1° C.;

Local flow velocity (U) computed from reduction of temperature and pressure data
Precision/sensitivity: $\varepsilon_U=[0.16; 6.2]\times10^{-4}$ m/s [2];

Volumetric flow rate (V) computed from U and known area (A)/radius (R) of circular cross-section where measurements are taken: $\dot{V}=AU=\pi R^2 U$
Precision/sensitivity in volumetric flow rate: $\varepsilon_{\dot{V}}=\pi R^2 \varepsilon_U=[0.063; 2.44]\times10^{-8}$ m$^3$/s=[0.063; 2.44]$\times10^{-2}$ mL/s=[0.038; 1.46] SCCM=[0.038; 1.46]$\times10^{-3}$ SLPM
Assumptions: Fully developed flow at point of measurement; Absolute pressure measured approximately equal to atmospheric pressure;

Reported operating ranges for a manufactured instance of the present embodiment: Airflow rate—[−0.8; 0.8] L/s=[−800; 800] mL/s=[−48,000; 48,000] SCCM=[−48; 48] SLPM. Airflow temperature—[10; 50] C. Ambient temperature—[−20; 85] C. Ambient pressure—[0.5; 1.5] atm=[0.51; 1.52]$\times10^5$ Pa. Ambient humidity—[0; 95] %;

Device operation before, during and after data acquisition requires no input to the device itself, with all instructions/commands being input directly to the graphical user interface;

The software may enable bi-directional pressure and temperature data to be plotted and displayed in real-time or stored for later visualisation. Data visualisation via the graphical user interface, including options for plot zooming in and translation, allowed for comprehensive and detailed analysis of the data acquired. A log (.txt) file may be generated for data storage, containing the raw data for downstream post-processing;

Fast Data Acquisition: maximum sampling frequency=2 KHz; minimum time between samples 0.5 ms;

Low Cost, with inexpensively-produced sampling tube/housing/housing cover (e.g. UV-cured polyurethane-acrylic polymer);

Portability/Reduced size: ideal for delocalised/home-based monitoring with minimal discomfort for the patient.

The illustrated embodiment is designed as a standalone device, but according to further embodiments existing respirometry systems may be modified to include an arrangement according to the present invention potentially to allow for a more precise or faster airflow measurements to be made.

In the above-described embodiment, a constriction ratio of $A_1/A_2\sim2$ is employed; this area ratio may however be varied dependent upon the desired design sensitivity. According to an embodiment, the flow meter is provided with an array of sampling tubes of different constriction ratios, allowing the flow meter to be applied to a range of situations calling for different sensitivities. According to a further embodiment, a sampling tube may be provided having dynamically-varying geometry, which can change its internal dimensions in service, in order to adjust its sensitivity in response to signals received.

As noted above, the present invention is by no means limited to respirometers and respirometry. Rather, the present invention is applicable to flow meters in general. Embodiments of flow meters according to the present invention may for example include the following beneficial features:

A third pressure sensor to measure the absolute pressure within the sampling tube may for example be provided, to avoid the need to rely on the assumption that local pressure is the same as atmospheric (this may be less of an issue in respirometry, but will not necessarily be so in other applications);

Embodiments may for example be provided with a variable-geometry constriction. For example, a flow meter according to an embodiment of the present invention may be provided with a powered iris or other movable arrangement within its interior, to allow the internal profile of the sampling tube to be adjusted dynamically in use, for example under control of a microcontroller. This may involve altering the size of a constriction within the sampling tube and/or altering the size of another internal area within the sampling tube. In particular, by altering internal dimensions of the sampling tube the sensitivity of the flow meter may be dynamically adjusted depending on the measurements, for example driven by a microcontroller. This would significantly extend the range of use of the flow meter respirometer. This may extend to permitting the flow meter to operate as a null-reading system for even greater sensitivity;

A flow meter according to an embodiment of the present invention may for example be provided with a fourth pressure sensor to directly measure the head loss, allowing the user to specify either the desired accuracy or maximum allowable interference;

A flow meter according to an embodiment of the present invention may for example be provided with interchangeable sensor elements, to offer a wider product family (in terms of sensitivity versus full-scale range).

In the following, a further embodiment of a flow meter according to a present embodiment is compared to a conventional Venturi flow meter.

Figure 7A:
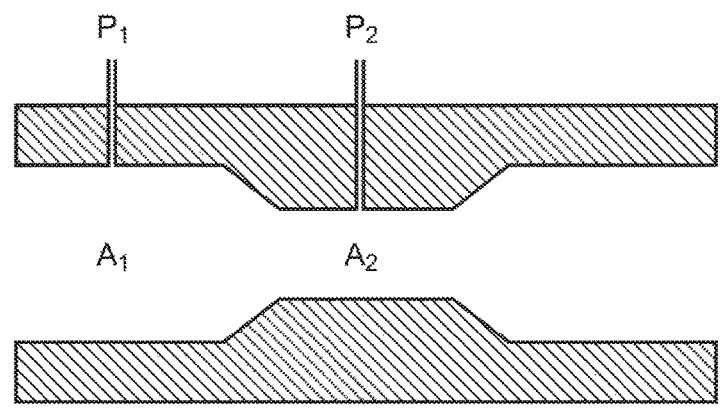
FIG. 7A is a schematic of the internal geometry and pressure sensing arrangement within a conventional Venturi tube.

The Venturi flow meter consists of a constriction installed within a pipe carrying a fluid. The static pressure of the fluid is sampled both upstream of the constriction and within the constriction using pressure ports flush with the interior walls of the tube (see FIG. 7A). Conservation of mass requires that the flow velocity increases as the cross-sectional area decreases, and conservation of energy requires that the pressure decreases as velocity increases. These relationships may therefore be used to infer the flow rate through the tube from the difference in the static pressures.

If it is assumed that the flow is incompressible (or, equivalently, that the flow velocities are reasonably low), then conservation of mass requires that $$Q = \overline{U}_1 A_1 = \overline{U}_2 A_2 \tag{1A}$$

where Q is the volumetric flow rate, A is the local area, the subscripts indicate the station (such that station 1 is upstream of the constriction and station 2 is in the constriction) and $\overline{U}$ is the mean cross-sectional velocity, such that $$\overline{U}_i = \frac{1}{A_i} \int_{A_i} u_i(r) dA \tag{2A}$$

where $u_i(r)$ is the local velocity profile at the station i, r is the distance from the centre of the tube, and the flow is assumed to be axisymmetric and in a direction parallel to the axis of the tube. Then, from conservation of energy, $$\int_{A_i} P_{0i}(r) dA = \int_{A_i} p_i(r) dA + \frac{\rho}{2} \int_{A_i} u_i(r)^2 dA \tag{3A}$$

where $P_{0i}(r)$ and $p_i(r)$ are the stagnation and static pressures, respectively, at some station i and which can both vary with r. If the flow is further assumed to be isentropic, then the stagnation pressure will be invariant with radius and station location, so $P_{01} = P_{02} = P_0$ for all r and $$P_0 = \frac{1}{A_i} \int_{A_i} p_i dA + \frac{\rho}{2A_i} \int_{A_i} u_i^2 dA \tag{4A}$$

where the functional dependences upon r have been omitted for clarity. Then, equating the stagnation pressures at stations 1 and 2 using equation (4A) and re-arranging, $$\frac{1}{A_1} \int_{A_1} p_1 dA - \frac{1}{A_2} \int_{A_2} p_2 dA = \frac{\rho}{2A_2} \int_{A_2} u_2^2 dA - \frac{\rho}{2A_1} \int_{A_1} u_1^2 dA \tag{5A}$$

With no further information available about the distributions of static pressure either with r or axial distance through the constriction, and no information about the form of the velocity profiles at stations 1 and 2, it is not possible to further simplify this expression. However, two correction factors $C_a$ and $C_b$ may be defined such that $$C_a^2 = \frac{1}{A_i P_i} \int_{A_i} p_i dA \tag{6A}$$

$$C_b^2 = \frac{1}{A_i \overline{U}_i^2} \int_{A_i} u_i^2 dA \tag{7A}$$

where $P_i$ is the static pressure measured at the wall of the tube. Then, if it is assumed that these correction factors are independent of the tube diameter and assuming that the velocity distributions have the same form at stations 1 and 2, equations (6A) and (7A) may be substituted into equation (5A) to yield, $$C_a^2(P_1 - P_2) = \frac{\rho}{2} C_b^2 (\overline{U}_2^2 - \overline{U}_1^2) \tag{8A}$$

Alternatively, the arbitrary coefficients $C_a$ and $C_b$ may be combined into a single 'discharge coefficient' C, such that $C = C_a/C_b$. Then, substituting equation (1A) into equation (8A), $$C^2(P_1 - P_2) = \frac{\rho}{2} \overline{U}_1^2 \left(\left(\frac{A_1}{A_2}\right)^2 - 1\right) \tag{9A}$$

Alternatively, by again substituting equation (1A), this can be expressed in terms of the volumetric flow rate as $$\frac{2}{\rho} \frac{P_1 - P_2}{Q^2} = \frac{1}{C^2} \left(\frac{1}{A_2^2} - \frac{1}{A_1^2}\right) \tag{10A}$$

Figure 8:
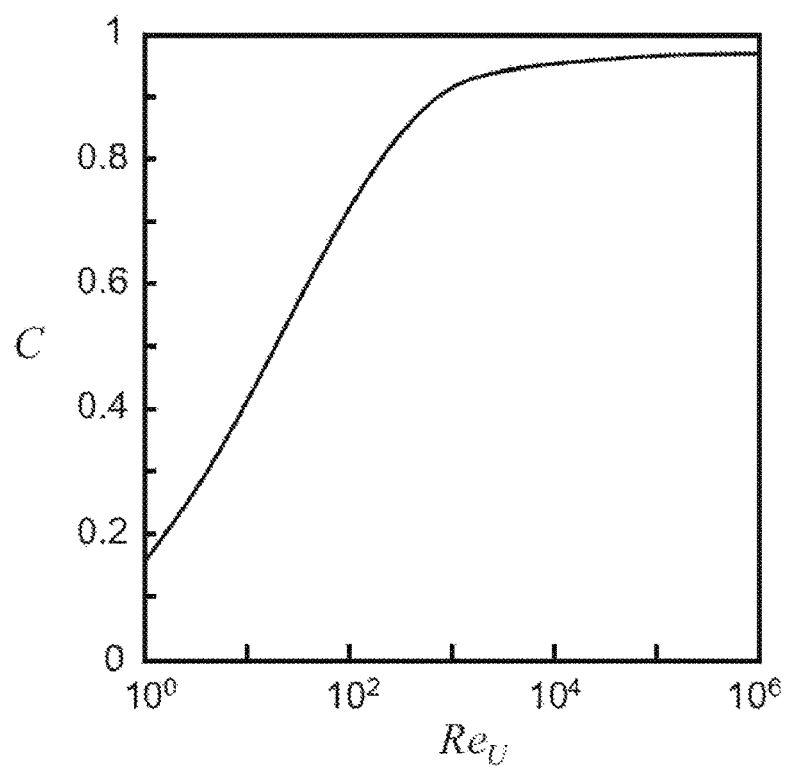
FIG. 8 illustrates the variation of discharge coefficient with Reynolds number for a typical Venturi flow meter (reproduced from Hollingshead, 2011)

The discharge coefficient C will vary with the flow Reynolds number $Re_U = 2\overline{U}R/\nu$ (where R is the tube radius and $\nu$ is the fluid kinematic viscosity) and will be sensitive to the constriction geometry. A typical variation of C with $Re_U$ for a generic Venturi meter is shown in FIG. 8 (reproduced from Hollingshead, C. L. (2011)—Discharge coefficient performance of Venturi, standard concentric orifice plate, v-cone and wedge flow meters at small Reynolds numbers. Technical Report 869, Utah State University, referred to herein as "Hollingshead (2011)", and the content of which is incorporated herein by reference in its entirety).

A Venturi meter of a given geometry would need to be calibrated using flows of known Q in order to obtain C using equation (10A). Then, with C and the geometry known, Q may be obtained from any pressure difference $P_1 - P_2$, which may be sampled using a single differential pressure sensor.

Since the highest pressure available in the tube is the stagnation pressure, any differential pressure-based flow meter sampling the stagnation pressure will necessarily be able to return the strongest possible signal. For isentropic flows (or those with negligible losses or heat transfer) the stagnation pressure is invariant through the tube and independent of geometry. However, the static pressure is not: P will decrease with increasing velocity, so a larger pressure difference $P_0 - P$ could be achieved by accelerating the flow in the vicinity of the static pressure port. The present embodiment, hereinafter referred to as a constricted stagnation meter, therefore seeks to (a) provide the strongest possible signal in low-velocity flows by sampling the difference between stagnation and static pressure directly; (b) accelerate the flow through a constriction in order to further increase the difference by reducing P, and (c) use the constriction to also condition the flow, achieving as uniform a velocity distribution as possible at the location of the stagnation port.

Figure 7B:
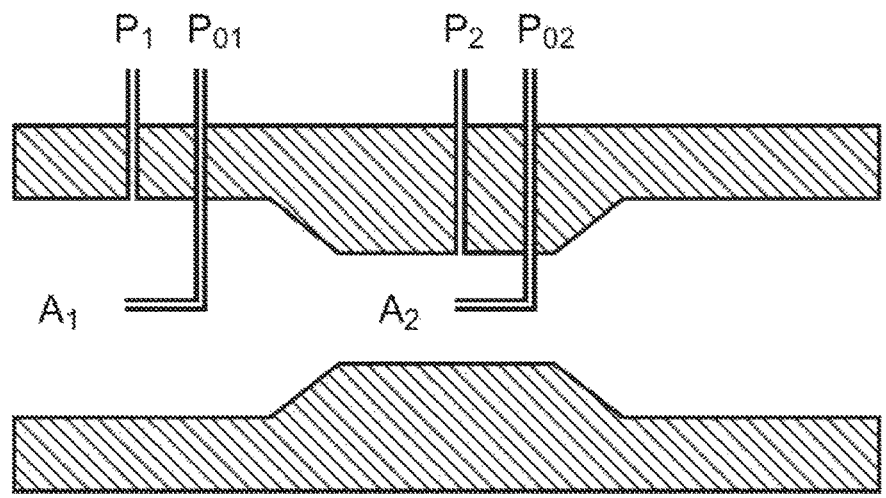
FIG. 7B is a schematic of the internal geometry and pressure sensing arrangement within a constricted stagnation arrangement flow meter according to a further embodiment of the present invention.

The constricted stagnation meter samples the stagnation pressure at the centre of the tube, together with the static pressure at an adjacent point on the wall of the tube; keeping the axial distance between the static and stagnation ports at a minimum reduces the effects of losses, thereby minimizing the variation in $P_0$. At the location of the tip of the stagnation probe at station 2 in FIG. 7B, $$P_0 = P_2 + \tfrac{1}{2}\rho U_2^2 \qquad (11A)$$

where $U_2$ is the velocity at the location of the stagnation port (on the tube centreline, where it is maximum). No assumption is required here about the form of $u_2/U_2$. However, the static pressure at the centreline is not available in this arrangement. If the static pressure instead is sampled at the tube wall rather than on the centreline, a small error will be introduced; this is equivalent to assuming that $C_a=1$ (a reasonable approximation). Then, equation (11A) can be re-arranged to yield $$\frac{2}{\rho}\frac{P_0 - P_2}{Q^2} = \frac{1}{A_2^2}\left(\frac{U_2}{\overline{U}_2}\right)^2 \qquad (12A)$$

again using equation (1A). The term $U/\overline{U}$ represents the ratio between the peak velocity at the centre of the tube and the spatially-averaged velocity. For laminar flows, the exact solution to the velocity distribution yields a parabolic profile with $U/\overline{U}=2$.

For the case of a very long, smooth uniform tube (or one in which the velocity profile is well-developed and invariant with axial position), then the velocity profile adheres reasonably well to the power law for turbulent pipe flows, $$\frac{u}{U} = (1 - r/R)^{1/n} \qquad (13A)$$

where n is a constant dependent upon Reynolds number. Then, substituting equation (13A) into equation (2A) and integrating yields (Shlichting, 1960)

$$\frac{U}{\overline{U}} = \frac{(n+1)(2n+1)}{2n^2} \qquad (14A)$$

For $Re_U \leq 2\times 10^4$, the power constant has been shown empirically to vary as (Fox, R. W., McDonald, A. T., and Pritchard, P. J. (2004), Introduction to Fluid Mechanics, Wiley, 2004, and the content of which is incorporated herein by reference in its entirety)

$$n \sim 0.782 \ln(Re_U) - 1.7 \qquad (15A)$$

Alternatively, for applicability at higher $Re_U$, the generalized Nikuradse velocity profile, $$\frac{U - u}{u_\tau} = 2.5 \ln\left(\frac{R}{R - r}\right) \qquad (16A)$$

(where $u_T$ is the wall shear velocity) may be substituted into equation (2A) and integrated to yield $$\frac{U}{\overline{U}} = 1 + B_0 \frac{u_\tau}{\overline{U}} \qquad (17A)$$

where $u_\tau$ is the wall shear velocity and $B_0=3.75$ is an analytically-determined constant; however, a value of $B_0=4.07$ provides a better fit to experimental data (Shlichting, 1960). Because the Nikuradse profile depends only upon the wall shear velocity, the Townsend similarity principle suggests that it may be extended to the more general case of tubes having non-smooth interior surfaces. Furthermore, the nondimensional friction parameter $\lambda$ is defined as $$\lambda = 8\left(\frac{u_\tau}{\overline{U}}\right)^2 \qquad (18A)$$

and is known to be well-represented by the solution to the transcendental $$\lambda^{-1/2} = 0.869 \ln(Re_U \lambda^{1/2}) - 0.8 \qquad (19A)$$

then, substituting equation (18A) into equation (17A), $$\frac{U}{\overline{U}} = 1 + 1.439 \lambda^{1/2} \qquad (20A)$$

where the functional relationship $A$ ($Re_U$) may be obtained numerically from equation (19A). The correction factor $(U/\overline{U})^2$ in equation (12A), as given by equations (14A) and (20A) is plotted in FIG. 9. For well-developed, statistically-stationary turbulent pipe flow, then, the stagnation pressure measured at the centre of the pipe may be related to the volumetric flow rate using equation (12A) and the semi-analytical calibration curve shown to within a high level of confidence. Alternatively (and more accurately), the constricted stagnation meter could be directly calibrated; this is preferable, as the constriction will necessarily result in a underdeveloped velocity profile.

Comparison of Techniques

The relative sensitivity K of a pressure-based flow meter may be expressed as $K = \Delta P/Q$, where $\Delta P$ is the pressure difference recorded by the sensors (in any given configuration), and a larger K indicates a more sensitive meter. Comparing the sensitivities of the Venturi-type meter and constricted stagnation meter for a given fluid, Q and fixed constriction ratio (and therefore head loss) using equations (10A) and (12A), $$\frac{K_0}{K_s} = C^2 \left(\frac{U_2}{\overline{U}_2}\right)^2 \left(1 - \left(\frac{A_2}{A_1}\right)^2\right)^{-1} \qquad (21A)$$

where $K_0$ and $K_s$ are the sensitivities of the constricted stagnation and Venturi meters, respectively.

The constricted stagnation meter will therefore be more sensitive than the Venturi meter if $K_0/K_s > 1$; this inequality is satisfied if and only if $$\left(\frac{A_2}{A_1}\right)^2 > 1 - \left(C\frac{U_2}{\overline{U}_2}\right)^2 \qquad (22A)$$

Since conservation of mass requires that $U \geq \overline{U}$ always, $C>1$ and the Venturi meter will only function if the condition $A_2<A_1$ is met, equation (22A) is always satisfied. Consequently, a constricted stagnation meter will always be more sensitive than a Venturi meter having the same head loss.

The importance of the constriction in improving the sensitivity can be shown by considering the sensitivity of the flow meter with no constriction. For illustrative purposes, the present constricted stagnation flow meter is illustrated as having stagnation and static ports in an unconstricted section of the tube (see $P_1$ and $P_{01}$ in FIG. 7B; in practice, these further stagnation and static ports would be omitted from the present embodiment). Then, from equation (12A), $$\frac{K_{02}}{K_{01}} = \left(\frac{A_1}{A_2} \frac{\overline{U}_1 U_2}{U_1 \overline{U}_2}\right)^2 \tag{23A}$$

However, $A_1 \overline{U}_1 = A_2 \overline{U}_2 = Q$ by definition, so $$\frac{K_{02}}{K_{01}} = \left(\frac{U_2}{U_1}\right)^2 \tag{24A}$$

Consequently, the sensitivity improvement for a given transducer will increase with the square of the ratio of centreline velocities. Alternatively, if it is assumed that $U/\overline{U}$ is constant (which is equivalent to assuming that the form of $u_1$ is the same as the form of $u_2$), equation (24A) may be re-expressed as $$\frac{K_{02}}{K_{01}} = \left(\frac{A_1}{A_2}\right)^2 \tag{25A}$$

and since $A_2<A_1$, the constricted stagnation meter will always be more sensitive than an unconstricted one.

Uncertainty Considerations

The above arguments have all assumed that the flow within the constricted section of the tube is well-developed. However, constrictions typically have the effect of significantly increasing the flow uniformity, as the acceleration will reduce the boundary layer thickness. Consequently, the correction $U/\overline{U}$ will be smaller than that predicted and shown in FIG. 9.

Figure 9:
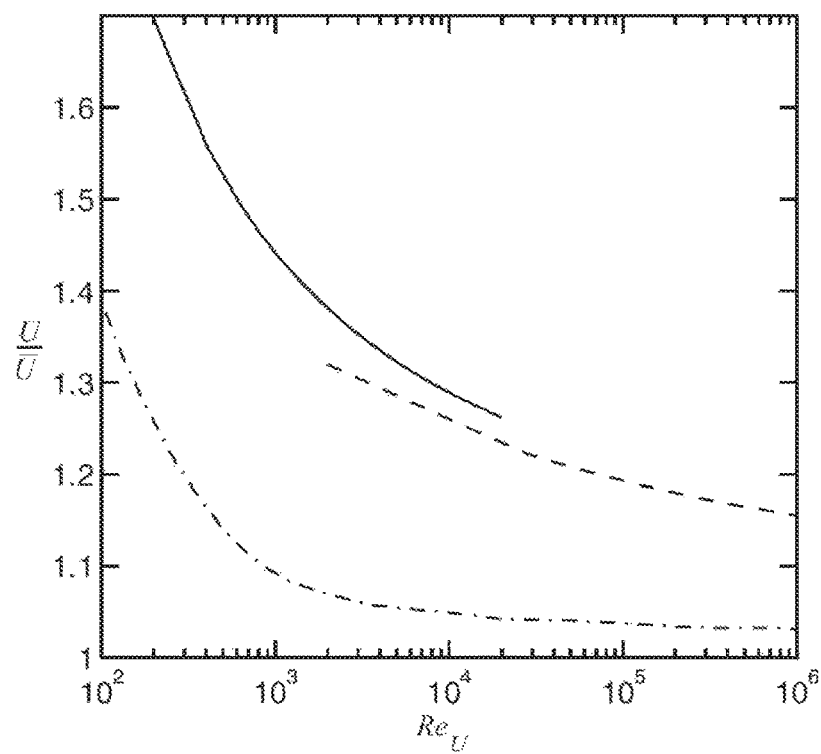
FIG. 9 illustrates approximation error in using central stagnation pressure in well-developed turbulent pipe flow. Solid line, Equation 14A; dashed line, Equation 20A; dash-dot line, data from Hollingshead, 2011, for comparison.

Comparing equations (10A) and (12A), it emerges that both the Venturi and constricted stagnation meter configurations require an empirical correction factor which depends upon the local velocity (and pressure) profiles; these are $1/C^2$ and $(U/\overline{U})^2$, respectively ($1/C$ for a typical Venturi meter has been included in FIG. 9 for comparison). The accuracy and repeatability of the flow meter will then depend strongly upon the uncertainty in these calibration factors and their sensitivity to error.

Only two assumptions were required for the case of the constricted stagnation meter: that the static pressure is invariant across the cross-section, and that the correction factor (U/U) varies only with Reynolds number. For the case of the Venturi meter, the correction factors $C_a$ and $C_b$ require greater approximations—namely, that the flow is isentropic between the stations 1 and 2 (which it cannot be through a constriction) and that the velocity profiles at stations 1 and 2 are of the same form (also unlikely, if the flow at station 1 is well-developed and the constricted section is short). Necessarily, then, greater uncertainty is expected in the calibration of the Venturi meter.

A second consideration is the sensitivity to uncertainty (or non-uniformity) in the velocity profile. Both the Venturi and constricted stagnation meters require some assumption about the uniformity of the static pressure over the cross-sectional area; this is a fairly reasonable approximation. However, the Venturi meter's velocity profile correction term $C_b$ depends upon the second area moment of velocity, while the constricted stagnation meter's correction depends only upon the first moment (or $\overline{U}$). Consequently, the amplification of uncertainty through the calibration process will be significantly less for the constricted stagnation meter.

Furthermore, if the tube itself is short (so that the inlet flow is not fully-developed and turbulent at the beginning of the constriction), the uncertainties would be further affected. Results presented by both Shlichting (1960) and Mohanty, A. K. and Asthana, S. B. L. (1978), Laminar flow in the entrance region of a smooth pipe, J. Fluid Mech., 90(3), 433-447 (the content of which is incorporated herein by reference in its entirety), taken together, suggest that even modest accelerations into short constrictions can significantly reduce the area variation in u(r), and that the inlet lengths required to develop the flow are fairly large relative to the tube radius. Furthermore, the assumptions that $C_a$ and $C_b$ are invariant with axial distance would necessarily fail.

Use of Flow Meter for Detection and Analysis of Heart Function

Figure 10:
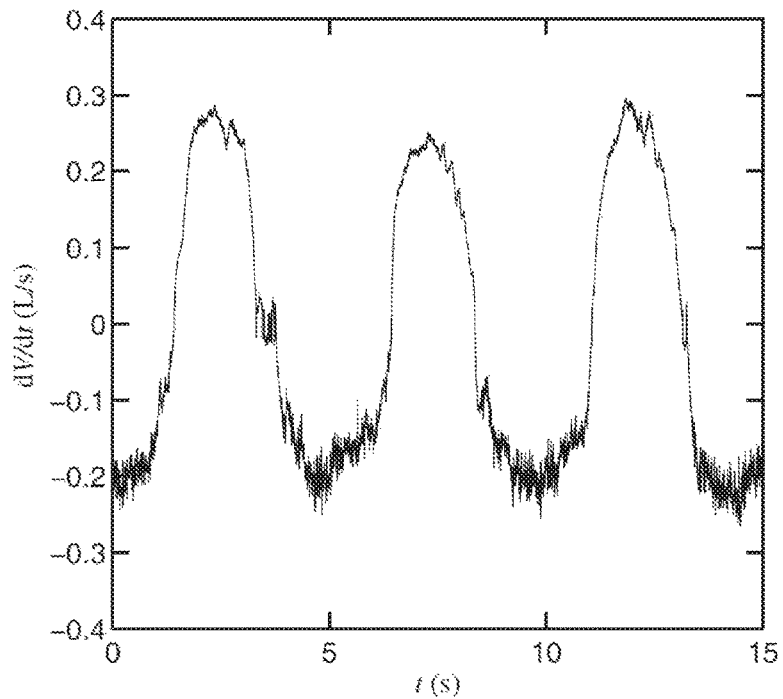
FIG. 10 shows the lung volumetric flow rate of a subject (Subject 2), recorded using the flow meter of the present invention for heart rate detection.

It has been found that the flow meter of the present invention is suitable for use in the detection and analysis of heart function Validation FIG. 10 shows independently-recorded volumetric flow rate through the lungs, as recorded by a respirometer according to the present invention. FIG. 10 shows the lung volumetric flow rate of a subject using the respirometer of the present invention and can be seen to be a periodic trace with a dominant mode at a frequency ($f_r$) of approximately 0.23 Hz, which corresponds to the breathing cycle of the subject; however, the trace also shows a substantial amount of energy contained at higher frequencies. The higher-frequency content of the trace shown in FIG. 10 is attributed to turbulence within the subject's airways rather than to signal noise; for example, the turbulence levels observed may be due to turbulence within the air exiting the subject's airway, or the result of poor conditioning of the inlet flow.

It is assumed that the "rest" volume of air $V_0$ within the subject's lungs remains constant, such that the net volume change $\Delta V$ may be approximated as shown in Equation 26A, where v is the signed volumetric flow rate, T is the respiratory wavelength and n is the integer number of breaths taken:

$$\Delta V \approx \int_0^{nT} \dot{v}(t) dt, \tag{26A}$$

For sufficiently long sample times, $\Delta V \to 0$. Similarly, an average breath volume may be defined as set out in Equation 27A:

$$V_n \approx \frac{1}{2n} \int_0^{nT} |\dot{v}(t)| dt. \tag{27A}$$

$\Delta V$ and $V_n$ for the tests carried out on three human subjects (Subject 1, Subject 2 and Subject 3) are shown in the below-referenced table and the results were found to be consistent with $\Delta V/V_n$ less than approximately 0.3.

|  | ΔV (L) | $V_n$ (L) | n |
| --- | --- | --- | --- |
| Subject 1 | 0.13 | 0.56 | 4 |
| Subject 2 | −0.11 | 0.40 | 5 |
| Subject 3 | −0.01 | 0.49 | 7 |

Conditions of Testing

In order to assess the use of the flow meter for heart rate detection, test data was collected from three subjects. Subjects at rest were required to breathe normally through the breathing tube of a respirometer, constructed in accordance with the present invention. The subject's heart function was monitored simultaneously, with an independent measurement system not synchronised with the respirometer clock (precluding correlational analysis). Further testing was also carried out with a modified breathing tube, adapted to enable the introduction of a blockage to simulate respiratory obstruction. Tests were typically carried out with the subject's nose pinched closed.

Results of Testing—Heart Function

The heart function detection feature of the present invention enables a user to obtain a measure of the "displacement" of the heart during a beat; for example, as the heart presses against the lungs. The present invention offers a non-intrusive measurement technique. The detection of the "displacement" of the heart can also be provided as a measure of the blood pressure in the lungs, detectable by the respirometer of the present invention.

It is envisaged that any necessary signal processing, to allow the respirometer to be used to detect heart function, can be provided external to the respirometer. However, in alternative embodiments the signal processing components are provided within the respirometer device.

Figure 11:
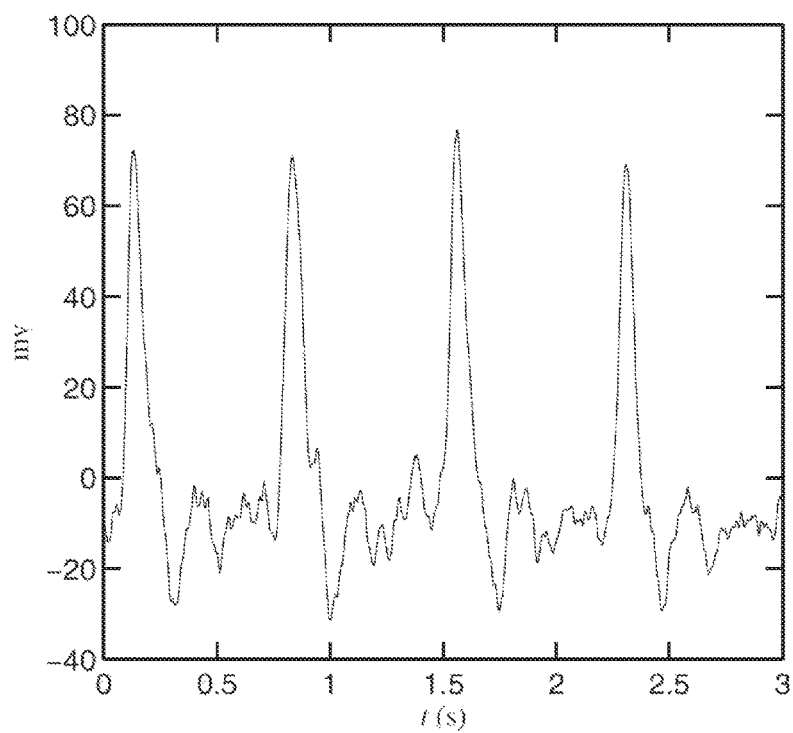
FIG. 11 shows the heart function of the same subject (Subject 2) referred to in FIG. 10.

FIG. 11 shows a typical plot of uncalibrated ECG outputs as a function of time. The ECG signal was uncalibrated, so the amplitudes shown in FIG. 11 are considered only as relative. The signal shown in FIG. 11 is clearly periodic with a dominant frequency of $f_h \approx 1.5$ Hz and exhibits a form that is consistent with those of a healthy adult.

Figure 12:
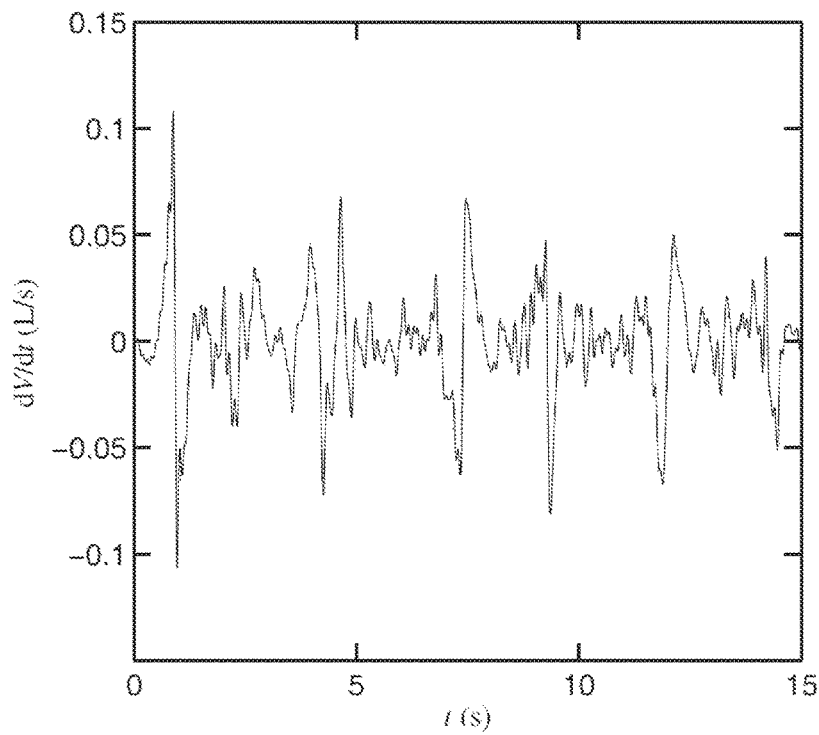
FIG. 12 shows the filtered lung volumetric flow rate of the same subject (Subject 2) referred to in FIGS. 10 and 11.

The extent to which the subject's heart rate was affecting their respiration was then assessed. It was found that the respiratory function of the subject is dominated by the low-frequency component, thus the respiratory signal, as shown in FIG. 10, was band-pass filtered in order to specifically attenuate both the very-low frequency components (the tidal breath mode) and the higher-frequency fluctuations associated with the flow turbulence. A standard equiripple finite-impulse response filter was applied to the data, having a pass band from 1.2 Hz to 10 Hz. FIG. 12 shows the filtered signal and no clear, dominant modes are evident.

Figure 13:
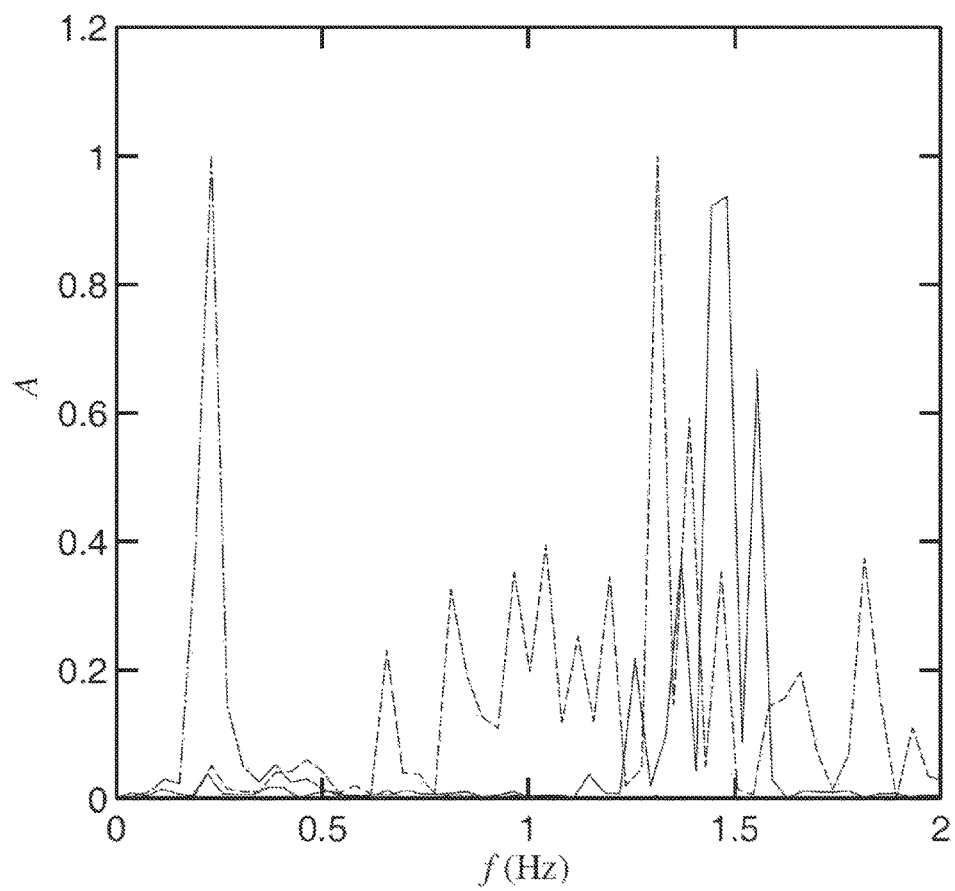
FIG. 13 shows a normalized Fourier transform of the signals collected from the same subject (Subject 2) referred to in FIGS. 10, 11 and 12, showing traces for heart signal (solid line), respirometer signal (dash-dot line) and band-pass filtered respirometer signal (dashed line)
Figure 14:
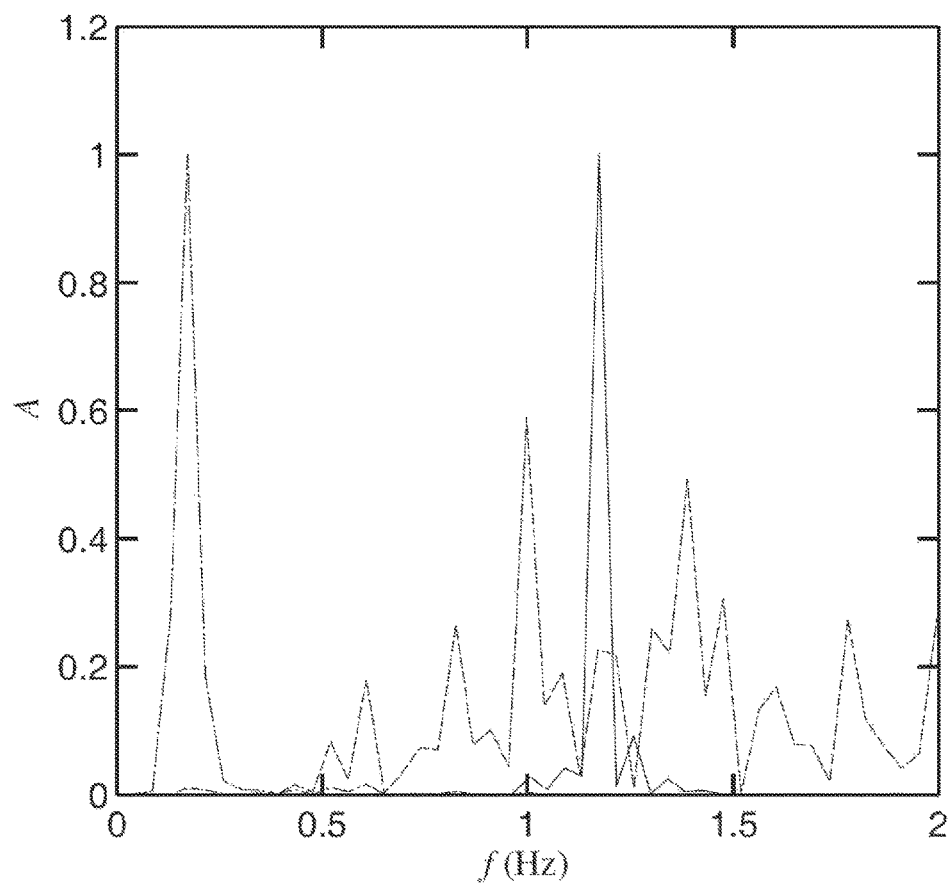
FIG. 14 shows a normalized Fourier transform of the signals collected from another subject (Subject 1), showing traces for heart signal (solid line), respirometer signal (dash-dot line) and band-pass filtered respirometer signal (dashed line)
Figure 15:
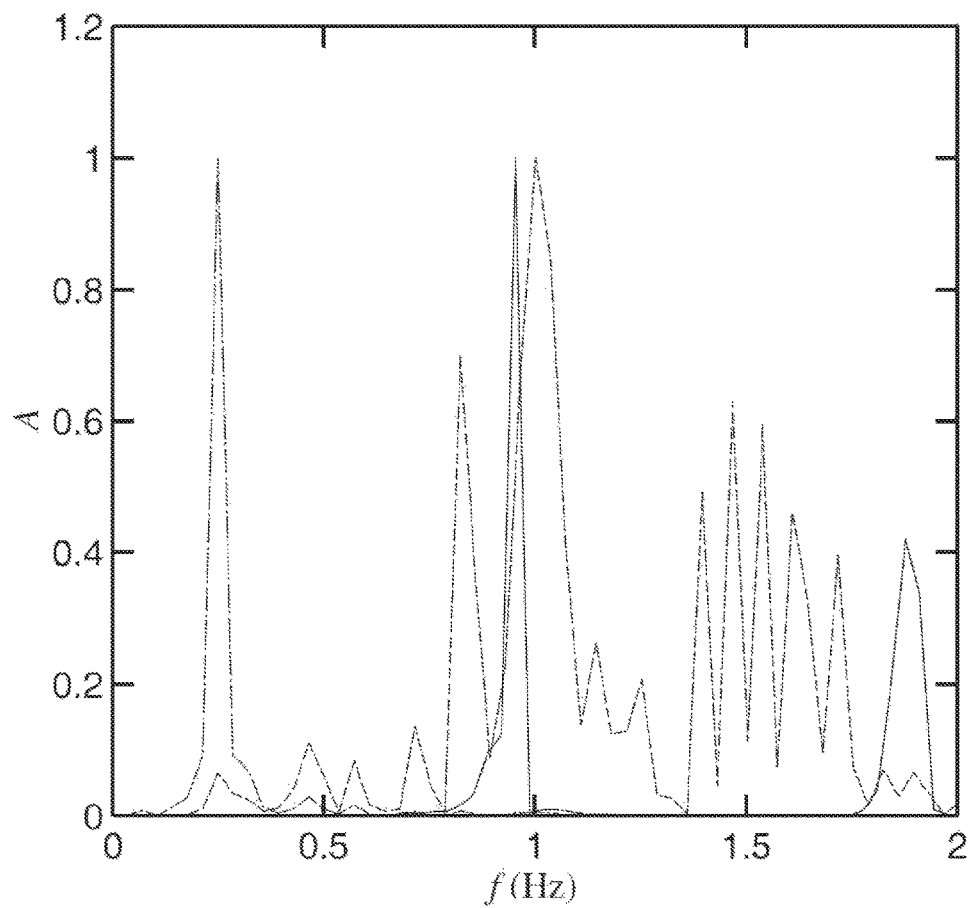
FIG. 15 shows a normalized Fourier transform of the signals collected from a third subject (Subject 3), showing traces for heart signal (solid line), respirometer signal (dash-dot line) and band-pass filtered respirometer signal (dashed line)

The spectral contents of the signals were then examined in detail. FIG. 13 shows the self-scaled magnitudes of the discrete Fourier transform of the signals collected from "subject 2", as referred to in FIGS. 10 and 11. The detected heart rate signal, shown in FIG. 13, clearly shows a dominant mode at the measured heart rate $f_h$, although with distribution, which was thought likely to be a result of an inconsistent wavelength. FIG. 13 also shows the unfiltered respirometer signal, which exhibits a clear mode at a frequency of $f_r$. FIG. 13 shows a band-pass filtered respirometer signal, which is significantly reduced in magnitude owing to the attenuation of the domination; however, for clarity this reduction is not shown and the plot of FIG. 13 has been re-scaled. Despite the decreased signal/noise ratio, a clear mode emerges at a frequency consistent with the recorded heart rate. The same analysis, as described with respect to FIG. 13, is shown for subject 1 and subject 3 in FIGS. 14 and 15, respectively. The results suggest that the correlation between the filtered respirometer signal and the heart rate detected in the case on subject 2 was not spurious.

Thus, the flow meter of the present invention can be accurately used for heart rate detection, and the dimensional amplitude of this signal component may be used as a measure of heart function.

Results of Testing—Obstructed Airway

Further measurements were collected using the respirometer of the present invention, using a modified breathing tube that was fitted with a device to simulate respiratory obstruction. Obstructions of 0%, 50%, 75% and 95% were simulated, wherein the 0% obstruction represented the modified breathing tube, but with the obstruction itself disabled to allow for the effects of modification alone to be quantified.

Figure 16:
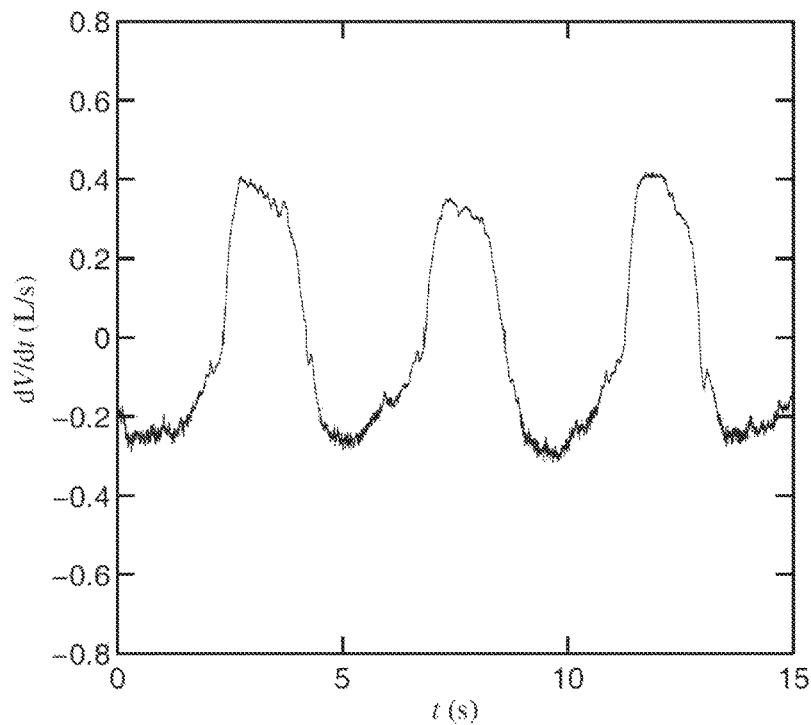
FIG. 16 shows lung flow rate for the same subject (Subject 2) as referred to in FIGS. 10, 11 and 12, using a modified breathing tube with 0% blockage.
Figure 17:
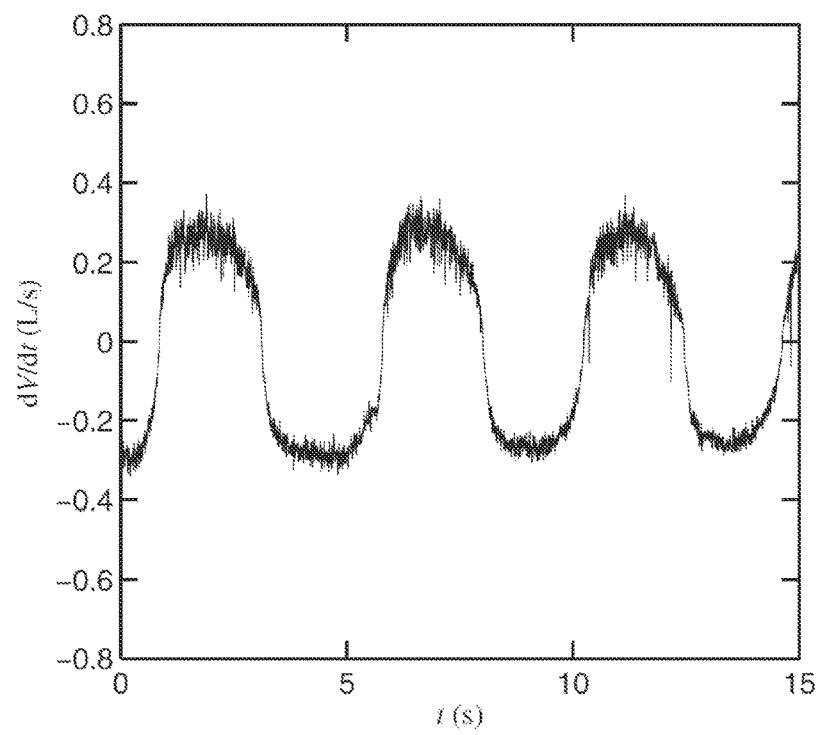
FIG. 17 shows lung flow rate for the same subject (Subject 2) as referred to in FIGS. 10, 11 and 12, using a modified breathing tube with 95% blockage.
Figure 18:
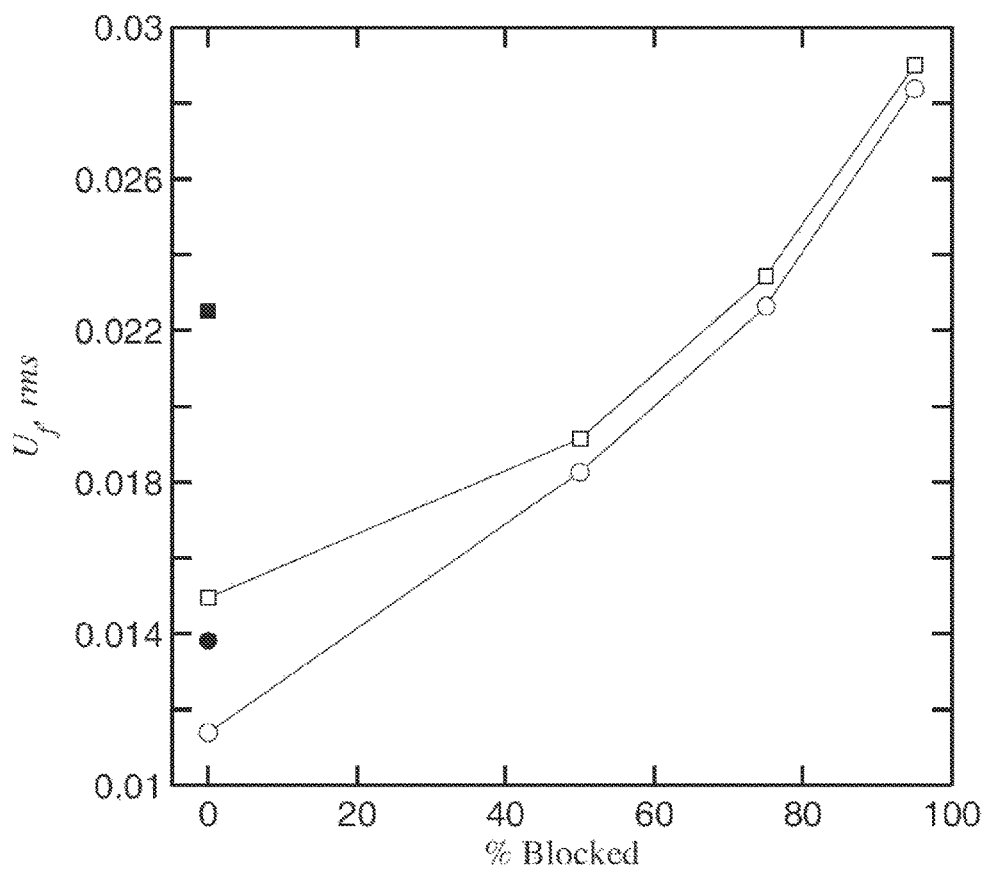
FIG. 18 shows the root-mean square of the high-pass filtered flow rate signals as a function of blockage ratio for Subject 2 of FIGS. 10, 11 and 12 (circles) and Subject 3 of FIG. 15 (squares), showing the results for the modified breathing tube (open symbols) and the unmodified breathing tube (filled symbols)

FIGS. 16 and 17 show the 0% and 95% blockage testing for a subject (subject 2) with lung flow rate (L/s) plotted against time (seconds). Although the cyclic breathing pattern of the subject remained relatively unaffected by the blockage, the results showed evidence of a greater amount of energy in the higher frequencies. In order to quantify this result, the flow rates were high-pass filtered at 3 Hz (as before, using an equiripple finite-impulse response filter) and the root-mean-square of the flow rates was calculated. FIG. 18 shows the results of the root-mean square of the high-pass filtered flow rates as a function of blockage ratio for subject 2 and subject 3. The results obtained from subject 1 were corrupted and are not shown. Referring to FIG. 18, a clear trend emerges.

Figure 19:
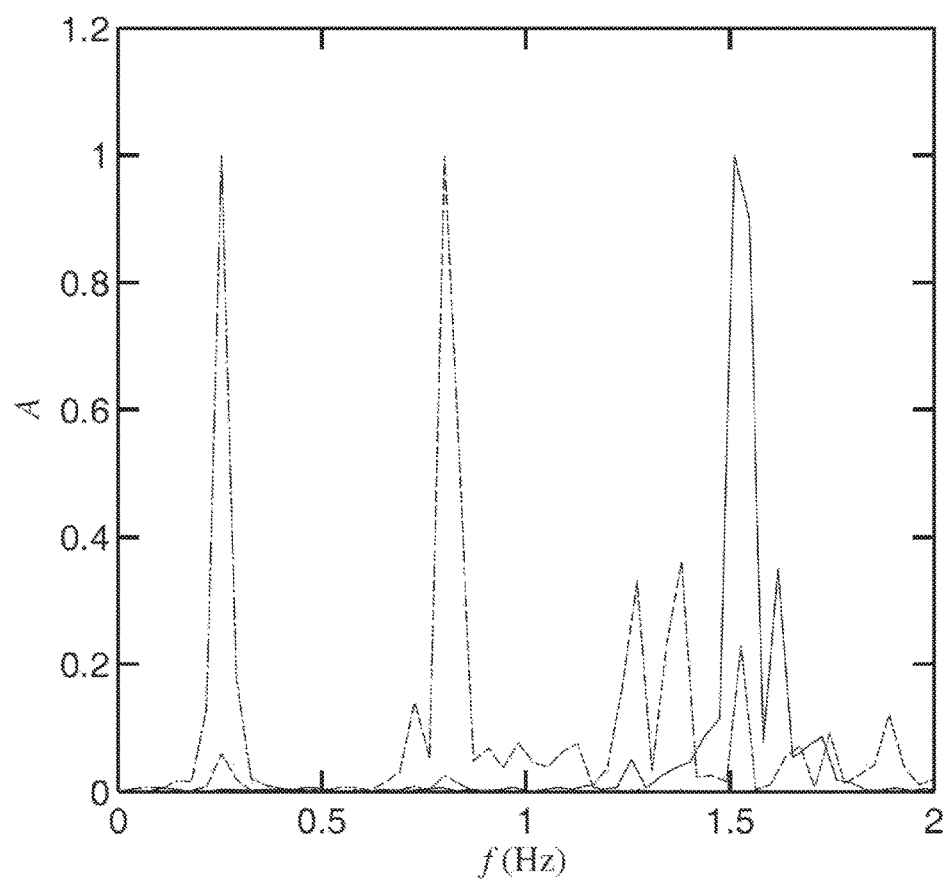
FIG. 19 shows a normalized Fourier transform of the signals collected for the subject (Subject 2) of FIGS. 10, 11, 12, with a 75% blockage, showing heart signal (solid line), respirometer signal (dash-dot line) and band-pass filtered respirometer signal (dashed line).

Referring to FIG. 19, the spectral decomposition of the heart rate monitor signal, the respirometer signal and the band-pass filtered respirometer signal are shown, for subject 2 with a 75% blockage. FIG. 19 shows that, in some cases, the filtering and FFT process returned a spike at the sub-harmonic of the heart rate. In most other cases, the method worked as previously described with respect to subject testing without blockages. It is thought that the sub-harmonic shown in FIG. 19 may have been an artefact of a poorly-tuned signal processing algorithm.

Within this specification, the term "about" means plus or minus 20%, more preferably plus or minus 10%, even more preferably plus or minus 5%, most preferably plus or minus 2%.

Within this specification, the term "subject" refers to an animal, preferably a mammal and most preferably a human.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

The invention claimed is:

1. A flow meter comprising:
    a sampling tube through which fluid may flow and a sensor arrangement, wherein the sampling tube comprises a first hollow section having a first internal cross-sectional area and a second hollow section having a second internal cross-sectional area being less than the first internal cross-sectional area;
    wherein the sensor arrangement is for measuring the a difference between stagnation and static pressures within a constriction of the second hollow section;
    wherein the sensor arrangement comprises one or more stagnation pressure measurement ports located within the second hollow section adjacent to one or more static pressure measurement ports;

and each static pressure measurement port is located at a longitudinal position within the sampling tube adjacent to each stagnation pressure measurement port.

2. The flow meter according to claim 1, wherein the sensor arrangement comprises two stagnation pressure measurement ports located within the second hollow section and facing in opposite directions.

3. The flow meter according to claim 1, wherein the sensor arrangement further comprises sensor circuitry located within a housing.

4. The flow meter according to claim 3, wherein each of the one or more stagnation pressure measurement ports is in communication with the sensor circuitry via one or more channels formed integrally in a wall of the housing.

5. The flow meter according to claim 1, wherein each of the one or more stagnation pressure measurement ports is provided at an end of a respective stagnation pressure measurement tube integrally formed with the housing.

6. The flow meter according to claim 5, wherein each of the one or more stagnation pressure measurement tubes extends upwardly from an exterior surface of the wall of the housing and the sensor circuitry is located adjacent an interior surface of the wall, directly underneath the one or more stagnation pressure measurement tubes.

7. The flow meter according to claim 1, wherein the sensor arrangement further comprises a temperature sensor for measuring temperature within the second hollow section.

8. The flow meter according to claim 1, wherein the sampling tube is provided with at least one interior surface defining at least part of an interior profile of the sampling tube and which is movable between at least a first condition and a second condition to alter an interior profile of the sampling tube.

9. The flow meter according to claim 1, further comprising a pressure transducer adjacent to the sampling tube for direct measurement of absolute pressures within the sampling tube.

10. A flow meter system, comprising:
the flow meter according to claim 1, wherein the sampling tube comprises a first sampling tube of the flow meter system; and
a second sampling tube through which a fluid may flow, interchangeable with the first sampling tube.

11. The flow meter system of claim 10, wherein the first and second sampling tubes present different internal profiles.

12. A fluid flow measurement method, comprising: obtaining pressure measurements relating to the pressure of fluid within a sampling tube of a flow meter according to claim 1.

13. The method according to claim 12, further comprising measuring a temperature of a fluid within the sampling tube.

14. The method according to claim 12, further comprising determining a volumetric flow rate of fluid flow within the sampling tube based at least in part upon pressure and/or temperature measurements.

15. The method according to claim 12, further comprising determining a mass flow rate of fluid within the sampling tube based at least in part upon the pressure and/or temperature measurements.

16. The method according to claim 12, further comprising detecting heart function of a subject according to a flow rate detected.

\* \* \* \* \*